United States Patent
Pot et al.

(10) Patent No.: US 11,918,683 B2
(45) Date of Patent: *Mar. 5, 2024

(54) TREATMENT OF IMMUNE DISEASES BY ADMINISTRATION OF ANTIGEN-SPECIFIC FORMULATIONS

(71) Applicant: Allero Therapeutics B.V., Rotterdam (NL)

(72) Inventors: Emil Richard George Pot, Ghent (BE); Cornelis Johannes Leenhouts, Haren (NL); Poul Sörensen, Meudon (FR)

(73) Assignee: Allero Therapeutics B.V., Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/072,772

(22) Filed: Dec. 1, 2022

(65) Prior Publication Data

US 2023/0149305 A1    May 18, 2023

Related U.S. Application Data

(62) Division of application No. 16/758,076, filed as application No. PCT/EP2018/079246 on Oct. 25, 2018, now Pat. No. 11,547,662.

(30) Foreign Application Priority Data

Oct. 25, 2017   (EP) ..................................... 17020500

(51) Int. Cl.
   *A61K 9/00*        (2006.01)
   *A61K 35/741*      (2015.01)
   *A61K 47/69*       (2017.01)

(52) U.S. Cl.
   CPC ............ *A61K 9/006* (2013.01); *A61K 35/741* (2013.01); *A61K 47/6903* (2017.08)

(58) Field of Classification Search
   CPC ... A61K 9/006; A61K 47/6903; A61K 35/741
   See application file for complete search history.

(56) References Cited

U.S. PATENT DOCUMENTS 11,547,662 B2 *   1/2023   Pot .......................... A61K 39/35

FOREIGN PATENT DOCUMENTS

| WO | WO01/66136 A2 | 9/2001 | |
| WO | WO-0166136 A2 * | 9/2001 | ............. A61K 39/35 |
| WO | WO2008/090223 A2 | 7/2008 | |
| WO | WO2012/128628 A1 | 9/2012 | |

OTHER PUBLICATIONS

Songwe Fanuel et al: "Decorating and loading ghosts with allergens for allergen immunotherapy: Human Vaccines & Inmunotherapeutics: vol. 13, No. 10", Human Vaccines & Immunotherapeutics, (Sep. 21, 2017), pp. 2428-2433.
Bosma T et al: "Novel surface display system for proteins on non-genetically modified gram-positive bacteria", Applied and Environmental Microbiology, American Society for Microbiology, US, vol. 72, No. 1, (Jan. 1, 2006), pp. 880-889.
P. Moingeon et al: "Enhancing Allergen-Presentation Platforms for Sublingual Immunotherapy", The Journal of Allergy and Clinical Immunology : An Official Journal of AAAAI, American Academy of Allergy Asthma & Immunology, vol. 5, No. 1, (Jan. 1, 2017) pp. 23-31.
Li et al: "Persistent protective effect of heat-killed *Escherichia coli* producing engineered, recombinant peanut proteins in a murine model of peanut allergy", Journal of Allergy and Clinical Immuno, vol. 112, No. 1, (Jul. 1, 2003), pp. 159-167.
Hsiao, Kuang-Chih, et al. "Long-term clinical and immunological effects of probiotic and peanut oral immunotherapy after treatment cessation: 4-year follow-up of a randomised, double-blind, placebo-controlled trial." The Lancet Child & Adolescent Health 1.2 (2017): 97-105.
Takiishi, Tatiana, et al. "Reversal of autoimmune diabetes by restoration of antigen-specific tolerance using genetically modified Lactococcus lactis in mice." The Journal of clinical investigation 122.5 (2012): 1717-1725.
Huibregtse, Inge L., et al. "Induction of antigen-specific tolerance by oral administration of Lactococcus lactis delivered Immunodominant DQ8-restricted gliadin peptide in sensitized nonobese diabetic Ab Dq8 transgenic mice." The Journal of Immunology 183.4 (2009): 2390-2396.
Huibregtse, Inge L., et al. "Induction of ovalbumin-specific tolerance by oral administration of Lactococcus lactis secreting ovalbumin." Gastroenterology 133.2 (2007): 517-528.
Allam, Jean-Pierre, et al. "Phl p 5 resorption in human oral mucosa leads to dose-dependent and time-dependent allergen binding by oral mucosal Langerhans cells, attenuates their maturation, and enhances their migratory and TGF-pi and IL-10-producing properties." Journal of Allergy and Clinical Immunology 126.3 (2010): 638-645.
Mucida, Daniel et al "Oral tolerance in the absence of natuarally occuring Tregs." The Journal of clinical investigation 115.7(2005): 1923-1933.
Mayer, Lloyd, and Ling Shao: "Therapeutic potential or oral tolerance." Nature Reviews Immunology 4.6 (2004): 407-419.

(Continued)

*Primary Examiner* — Blessing M Fubara
(74) *Attorney, Agent, or Firm* — N.V. Nederlandsch Octrooibureau

(57) ABSTRACT

The present invention relates to the treatment of autoimmune and allergic diseases by oromucosal administration of a formulation consisting of an optimized combination of antigen, tolerizing agent and mucoadhesive carrier for each immune disease indication.

10 Claims, No Drawings

Specification includes a Sequence Listing.

(56) References Cited

OTHER PUBLICATIONS

Masek Josef et al: "Multi-layered nanofibrous mucoadhesive films for buccal and sublingual administration of drug-delivery and vaccination nanoparticles—important step towards effective mucosal vaccines", Journal of Controlled Release, Elsevier, Amsterdam, NL, vol. 249, Jul. 25, 2016 (Jul. 25, 2016), pp. 183-195, XP029927819, ISSN: 0168-3659, D0I: 10.1016/J.JCONREL.2016.07.036 abstract p. 184, left-hand column paragraph 1-paragraph 4.

* cited by examiner

TREATMENT OF IMMUNE DISEASES BY ADMINISTRATION OF ANTIGEN-SPECIFIC FORMULATIONS

REFERENCE TO AN ELECTRONIC SEQUENCE LISTING

The contents of the electronic sequence listing (sequence-listing.xml; Size: 5.94 Kb; and Date of Creation: Jan. 2, 2023) is herein incorporated by reference in its entirety.

FIELD OF THE INVENTION

The present invention relates to the fields of medicine and immunology. The present invention relates to the treatment of immune mediated disorders e.g. autoimmune and allergic diseases by administration of a formulation consisting of an optimized combination of antigen, tolerizing agent and mucoadhesive carrier for each immune disease indication.

STATE OF THE ART

The immune system has the task of distinguishing between self and non-self. The mucosal immune system, present along the respiratory, gastrointestinal and genitourinary tracts, has the additional burden of coexisting with an abundance of bacteria and innocuous antigens, such as food, airborne antigens or the commensally bacterial flora. A key feature of the mucosal immune system is its ability to remain tolerant to these antigens while retaining the capacity to repel pathogens effectively. Introduction of antigen systemically, whether by injection or injury, leads to local infiltration of inflammatory cells and specific immunoglobulin production. By contrast, antigens introduced at mucosal surfaces, such as in the oral cavity, gastrointestinal and genitourinary tracts, elicit active inhibition of the immune response to those antigens systemically. The specific induction of these regulated responses by administration of antigen through the mucosal surfaces of the oral cavity and gastrointestinal tract is known as oral tolerance. Oral administration of antigen can lead to systemic unresponsiveness and is an attractive alternative to immunosuppressive medical inventions that have undesirable side-effects (such as steroids). Tolerance inductions via the mucosa have been proposed as a disease modifying treatment strategy against autoimmune, allergic and inflammatory diseases.

The following discussion of the background of the invention is merely provided to aid the reader in understanding the invention and is not admitted to describe or constitute prior art to the present invention.

Immune mediated disorders such as autoimmune and allergic diseases or anti-drug antibodies (ADA) place a tremendous burden on the patient and society, resulting in decreased quality of life and huge costs. Moreover, no adequate treatment exists without acceptable side effects or which is socially appropriate. Current treatments for autoimmune diseases are largely palliative, generally immunosuppressive, or anti-inflammatory. Steroidal or NSAID treatment limits inflammatory symptoms of many autoimmune diseases. Intravenous immunoglobuline treatment is used for several auto-immune diseases. More specific immunomodulatory therapies, such as the TNFα antagonists etanercept, have been shown to be useful in treating rheumatoid arthritis (RA). Nevertheless, these immunotherapies may be associated with increased risk of adverse effects, such as increased susceptibility to infection. Celiac disease, an autoimmune-like immune mediated disorder which can be characterized by chronic small intestinal inflammation triggered by gluten (glutenin and gliadin), can only be effectively treated by a socially restrictive diet that requires lifelong abstinence from foods that contain wheat, rye or barley. While a strict gluten-free diet can lead to healing of the intestine, the intolerance to gluten is permanent.

Hence, induction of antigen specific-oral tolerance therapy would be an attractive therapeutic approach. Although oral tolerance was first described in 1911, it was not until the later 1970s that investigators started to address the mechanisms involved (Mayer and Shao, Nat Rev Immunol. 2004, 4:407-419). Several mechanisms have been proposed for the development of oral tolerance, ranging from the deletion of antigen-specific T-cells, over immune deviation and induction of anergy to suppression by Tregs (Mucida et al., J Clin Invest. 2005, 115:1923-1933). Targeted and more efficient delivery of molecules for therapeutic and prophylactic applications is a priority for the pharmaceutical industry. Effective strategies should reduce the required dose, increase safety and improve efficacy by focusing molecules at the desired site of action. Mucosal routes of drug and vaccine delivery offer a number of logistical and biological advantages compared with injection. Oromucosal delivery such as via sublingual or buccal routes is particularly attractive as a result of the ease of administration making it very relevant for individuals, e.g. children, who have difficulties swallowing tablets. Furthermore, in the context of immunotherapy, there is strong scientific rationale for the preventive benefits of targeting the developing immune system of children and immunotherapy via the oromucosal route would allow this.

In the context of allergen sublingual immunotherapy (SLIT) considerable progress has been achieved in the last few years regarding our understanding of the physiology of the oral immune system. This strengthened scientific background has confirmed the relevance of the sublingual route to induce antigen-specific tolerance and, furthermore, has pointed out to the interest of targeting oral antigen presenting cells such as dendritic cells (DCs) and Langerhans cells (oLC) to better mobilize allergen-specific regulatory immune mechanisms. It is now well established that SLIT is a safe oromucosal treatment for allergies, which is now broadly recognized as a valid alternative to subcutaneous immunotherapy (SCIT) and more than 20 years of clinical research has confirmed the relevance of the sublingual route to induce long term allergen-specific tolerance and disease modifying effects. The excellent safety profile of SLIT can be explained by the fact that oral tissues contain few pro-inflammatory cells such as mast cells and eosinophils and other danger signals and that the antigen-presenting cells (APCs) involved in the capture, processing of antigens and the subsequent presentation of derived peptides to naive T cells oral APCs exhibit a tolerogenic phenotype. As a consequence the default response initiated by oral APCs to antigens is tolerance allowing for the administration of intact whole antigens without any systemic inflammatory responses unlike the situation when administering via e.g intravenous, intracutaneous or intradermal routes. However, issues still remain regarding efficacy and the requirement for daily administrations over 3 years treatment leading to low compliance and adherence rates. An explanation for the low efficacy requiring a 3 years treatment could be the short retention time of the therapeutic agent when formulated in drops or tablets at the oral mucosa. Allam et al., (J Allergy Clin Immunol. 2010, 126:638-645) demonstrated in human oral mucosa a dose-dependent and time-dependent allergen binding by oral mucosal Langerhans cells (oLCs) indicating that dose strength determines AIT efficacy.

Innocuous bacteria that are used in fermented food products and probiotics have been shown to have antigen-specific tolerogenic properties and could therefore be used as tolerizing agent to enhance the efficacy of antigen-specific oromucosal immunotherapies (Huibregtse et al., Gastroenterolgy 2007, 133:517-528; Huibregtse et al., J. Immunology 2009, 183:2390-2396; Takiishi et al., J Clin Invest. 2012, 122:1717-1725; Hsiao, K-C et al., Lancet Child & Adolescent 2017, 1:97-105). Examples are the food lactic acid bacteria, such as *Lactococcus lactis* and *Lactobacillus rhamnosus*, or the probiotic bacterium *Escherichi coli* Nissle. However, the current approaches use live bacteria, which in some cases are also genetically modified to produce the antigen of interest in situ. Several disadvantages may be associated to such approaches, which can be practically of nature or can be a regulatory obstacle. Practical challenges may include: the need to keep the bacteria alive or viable in the formulation and during administration before reaching the target cells in the musosal tissue; limitations to the expression of the antigen by the recombinant bacterium; antigen degradation by host bacterial proteases; the requirement of a new master cell bank for every antigen-specific treatment. Regulatory challenges may include: difficulty to define the exact antigen dose; the presence of recombinant DNA; containment of the recombinant bacteria. Even if these practicalities and regulatory issues are overcome, e.g. by just mixing live non-recombinant bacteria with the antigen, the short retention time in the oral cavity of such formulations still limit the efficacy of the treatment and requires long treatment regimens. Hence, low compliance and adherence rates are still an issue.

Thus, there remains a problem in the art to effectively induce tolerance of antigens in general and to do this effectively through the oromucosal delivery route in particular.

SUMMARY OF THE INVENTION

Surprisingly, we found that an antigen that is causing an immune response in patients suffering from e.g. allergic rhinitis and allergic asthma, multiple sclerosis, type I diabetes, autoimmune uveitis, autoimmune thyroiditis, autoimmune myasthenia gravis, rheumatoid arthritis, pemphigus vulgaris, Sjögren's disease, neuromyelitis optica, food allergy or celiac disease, which is delivered via the oromucosal route when combined in a mucoadhesive carrier of hydrogels or electrospun fibers with non-living bacterial particles derived from food-grade lactic acid bacteria or probiotic bacteria, induced an antigen-specific and durable immune tolerance in short course treatments. We observed that the oromucosal administration of such an antigen by a formulation with non-living bacterial particles incorporated in said mucoadhesive hydrogels or electrospun fibers enables slow release, better presentation and extended exposure of the pharmaceutically active materials, and gives a significantly better suppression of the antigen-specific immune response in comparison to the oromucosal administration of said antigen alone or in only combination with said bacterial particles.

As a consequence, we also observed that the oromucosal administration of such an antigen by a formulation solely with non-living bacterial particles gives a significantly better suppression of the antigen-specific immune response in comparison to the oromucosal administration of said antigen alone.

We demonstrate that the embodiments of the invention can induce oral tolerance with much higher efficiency than with monotherapy with antigen or bacterial particles or mucoadhesive hydrogel/electrospun fibers alone. In vivo and ex vivo activation of antigen-specific regulatory T cells was strongly enhanced when administrating the antigen compositions according to the invention. Specifically, oromucosal administration of gliadin or gliadin derived peptides, which is immunodominant for DQ2 and/or DQ8 mediated T-cell responses by a combination of a mucoadhesive carrier of hydrogel/electrospun fibers and bacterial particles, induces suppression of local and systemic DQ2 and or DQ8 restricted T-cell responses. Treatment resulted in an antigen-specific decrease of the proliferative capacity of the splenocytes and lymph node cells, which was critically dependent on the production of IL-10 and TGF-β and associated with a significant induction of Foxp3+ regulatory T-cells. Because this approach of antigen-formulated bacterial particles in a mucosadhesive hydrogel/electrospun fiber carrier has the capacity for potentiating oral tolerance even in the setting of established hypersensitivity, it is applicable for the treatment of celiac disease and other autoimmune and/or allergic diseases. The efficacy of the invention was demonstrated in autoimmune and allergic disease models, as well as in the context of immune inactivation of biological therapeutics.

DETAILED DESCRIPTION OF THE INVENTION

Throughout this disclosure, various publications, patents and published patent specifications are referenced by an identifying citation. The disclosures of these publications, patents and published patent specifications are hereby incorporated by reference.

General Techniques

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular Cloning: A Laboratory Manual" Second Edition (Sambrook et al., 1989); "Oligonucleotide Synthesis" (M. J. Gait, ed., 1984); "Animal Cell Culture" (R. I. Freshney, ed., 1987); the series "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987, and periodicals) "Polymerase Chain Reaction" (Mullis et al., eds., 1994); and "Current Protocols in Immunology" (J. E. Coligan et al., eds., 1991).

Definitions

As used herein, certain terms may have the following defined meanings. As used in the specification and claims, the singular forms "a", "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of"

when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

Invention

We demonstrate that oromucosal administration of an immune dominant antigen presented and formulated with bacterial particals in a mucoadhesive patch, film or hydrogel induces superior suppression of local and systemic T-cell responses. Treatment resulted in an antigen-specific decrease of the proliferative capacity of the splenocytes and lymph node cells, which was critically dependent on the production of IL-10 and TGF-β and associated with a significant induction of Foxp3+ regulatory T-cells. This approach of antigen-formulated bacterial particals has the capacity for potentiating oral tolerance even in the setting of established hypersensitivity. Thus it is applicable for the treatment of celiac disease and other autoimmune and/or allergic diseases. The efficacy of the invention was demonstrated in autoimmune and allergic disease animal models, as well as in the context of human immune disorders derived ex vivo models.

The goal of the invention is achieved by means of preparation for administration of at least one antigen, preferably purified antigen, or biological material containing one or more antigens, whether or not combined with bacterial particles, below referred to as "antigen containing substance", incorporated in a mucoadhesive patch, film or hydrogel. In this way, the overall solubility and rate of dissolution of such antigen containing substance is made optimal by techniques know in the art in order to increase their bioavailability. The effect is most significant in variants, by which the antigen containing substance is incorporated directly in the material of the nanofibers, such as for example disclosed in WO 2014/131376 or electrohydrodynamically obtained fibres, such as for example disclosed in WO2015/189212 and to be formulated into a mucoadhesive patch, including but not limited to such mucoadhesive patch as disclosed in WO2012/097763 and WO2016/051159. In a preferred embodiment, the mucoadhesive patch is a patch as disclosed in WO2016/051159. In another embodiment of the invention, the antigen containing substance is formulated into bioadhesive films, such as for example in US2015125495 and WO2016/079246. In a further embodiment of the invention, the antigen containing substance is formulated into hydrogel matrices such as for example disclosed in "Advances in Physicochemical Properties of Biopolymers" Part 2 (Mansuelli & Renard, eds., 2017, eISBN: 978-1-68108-544-9), and preferably a biodegradable mucoadhesive hydrogel.

The most suitable biologically compatible material for production of the layers of the mucoadhesive patch, film or hydrogel is a biologically compatible polymer, especially polymer from group of polyvinyl alcohols (PVA), polylactides (PLA), polylactide-co-glycolides (PLGA), polycaprolactones (PCL), polyvinylpyrrolidones (PVP), polyurethanes (PUR), polyacrilic acid (PAA), their copolymers, cellulose derivatives such as for example hydroxypropyl cellulose (HPC), hydroxypropyl methycellulose (HPMC), polyethylene-oxide (PEO), polyethylene glycol/polyvinylcaprolactam/polyvinyl acetate copolymer, silk fibroin, chitosan-, alginate-, and hyaluronic acid derivatives, their mixtures as well as numerous polymerizable monomers, mixtures of at least two of these. To speed up the release of the antigen containing substance from the layers, it is possible to create the layer from biologically degradable material. The advantage of this variant is also that after and/or during the release of the antigen containing substance, the layer decomposes in the body of the recipient, so it is not necessary to remove it additionally.

In one embodiment, the polymer layers can also comprise plastisizers, such as polyols, phtalhates or citrates to enhance the plasticity of the layers, and/or absorption accelerators, such as acetylcysteine, surface active substances, chelating substances, fatty acids, polyols, dextran sulphates, sulfoxides, Azone®, (lyso)phosphatidylcholine, metoxysalicylate, menthol, aprotonin, dextran sulphate, cyclodextrins, 23-lauryl ether to facilitate the penetration of particles.

In a first aspect the invention relates to a mucoadhesive carrier comprising a non-living bacterial particle and an antigen for use in inducing immune tolerance to the antigen in a subject, wherein the mucoadhesive carrier is mucosally administered to the subject. Mucosal administration of the mucoadhesive carrier is understood to comprise contacting the mucoadhesive carrier to a mucous membrane or mucosa of the subject. It is further understood herein that induction of immune tolerance is herein understood to comprise increasing or enhancing an already existing (too weak) tolerance.

Preferably the invention relates to a method for inducing immune tolerance to an antigen, comprising oromucosal administration of said antigen by a bacterial particle-mucoadhesive patch, film or hydrogel formulation.

The terms "immune tolerance", "immunological tolerance", "tolerance" or "desensitise" are here defined as to make a sensitised or hypersensitive subject, less sensitive, insensitive or nonreactive to a given antigen for which the subject is to be tolerized by reducing the immunological reactivity of a subject towards the antigen. Immune tolerance may be generated, for example, by exposure of mucosal surfaces to tolerance-inducing antigen-BLP comprising mucoadhesive carrier compositions as defined herein. Mucosal administration of both high- and low-dose antigen may result in immune tolerance, in which the immune response to subsequent systemic administration of antigen is reduced. At least two mechanisms of immune tolerance may exist. Tolerance to high-doses of an antigen appears to occur by inactivation or clonal deletion of Th1 and Th2 cells. In contrast, tolerance to low doses of antigen leads to bystander immune Suppression mediated by stimulation of Treg cells to produce Suppressive cytokines Such as interleukin-4 (IL-4), interleukin-10 (IL-10) and TGF-β. See also Anderson and Jabri (Current Opinion in Immunology 2013, 25:410-417) and Rayner and Isaacs (Seminars in Arthritis & Rheumatism (2018), doi://doi.org/10.1016/j.semarthrit.2018.09.008).

Preferably the invention relates to the use of a bacterial partial-mucoadhesive patch, film or hydrogel formulation of an antigen for the preparation of a medicament, medical food or nutraceutical for oromucosal administration to treat an immune response related disease in a patient, wherein said antigen is released at the oromucosal tissue of said patient.

Preferably, said antigen is delivered by an antigen formulated in a bacterial particle-mucoadhesive patch, film or hydrogel.

Preferably, the present invention relates to the use of an antigen formulated with bacterial particles for the preparation of a medicament for oromucosal administration to induce immune tolerance.

Preferably, said immune tolerance is induced in a patient. Said patient is preferably a human or an animal. Said animal is preferably a mammal, and preferably chosen from the group consisting of mice, rats, rabbits, cats, dogs, pigs, cows, sheep, and horses. Preferably, said mammal is human. Preferably, said immune tolerance is mucosal tolerance.

Mucosa

Mucosa as used here can be any mucosa such as oral mucosa, rectal mucosa, urethral mucosa, vaginal mucosa, ocular mucosa, pulmonary mucosa and nasal mucosa.

Oromucosal administration as used throughout the application encompasses the targeted delivery to the oral mucosa. Oromucosal administration includes buccal, sublingual and gingival routes of delivery. Preferably, said oromucosal delivery is buccal or gingiva administration and said tolerance is oral tolerance.

Oromucosal tolerance as used here throughout the application is the inhibition of specific immune responsiveness to an antigen in an animal (including humans), after said animal has been exposed to said antigen via the oromucosal route. Preferably, said mucosal tolerance is systemic tolerance.

The present invention thus relates to a method or use as described herein, wherein said induction of immune tolerance is more effective at least 1.5, preferably 2, more preferably 3 times or more relative to before said induction. Alternatively, said antigen is better tolerated at least 1.5, 2, 3 times or more relative to before said induction. The induction of immune tolerance can be measured by methods known in the art. Preferably, said induction of immune tolerance can be measured by modulation of a cytokine level in said animal. As such, the modulation can be an increase of a cytokine level, for instance said increase of a cytokine level is at least 1.5, 2, 3 times or more relative to before said induction, e.g. IL-10 or TGF-β. Alternatively, said modulation is a decrease of the level of a particular cytokine level, for instance said decrease of the cytokine level is at least 1.5, 2, 3 times or more relative to before said induction, e.g. IL-12, IL-17 and IFN-γ. The cytokines which are modulated may be chosen from any relevant cytokines, preferably said cytokines are chosen from the group consisting of IL-2, IL-4, IL-5, IL-6, IL-8, IL-10, IL-12, IL-13, IL-17, IL-23, TNF-α, IFN-γ, IFN-α, MCP-1, TGF-β, RANK-L and Flt3L.

Tolerizing Compounds

In the present invention, the non-living bacterial particles stimulate the immune system to enhance antigen-specific tolerogenic immune responses, and at the same time may deliver the antigen at the intended site, e.g. the oral mucosa.

Tolerogenic compositions containing non-living bacterial partials according to the present invention may be prepared, tested for immunogenicity, efficacy and safety employing the technology disclosed in published PCT application WO 02/101026, hereby incorporated by reference.

Preferably, the non-living bacterial particle for use in accordance with the invention is derived from a probiotic bacterium. More preferably the non-living bacterial particle is derived from a (probiotic) *Lactobacillius*, a *Lactococcus*, a *Bifidobacterium* or an *Escherichia coli* Nissle. Most the non-living bacterial particle for use in accordance with the invention is derived from at least one of *Lactococcus lactis* MG1363, *Lactobacillus rhamnosus* GG and *Escherichia coli* Nissle 1917.

Antigen containing formulations may be based on particles derived from inactivated *Lactococcus lactis* bacteria, a safe bacterium traditionally used in the food industry, such as for the production of cheese (the particles are elsewhere described as Gram-positive Enhancer Matrix or Bacterium-Like Particles and are herein referred to as "BLPs"). BLPs activate the innate immune systems through Toll-like receptor 2 (TLR2; Ramirez et al., Mucosal Immunology 2010, 3:159-171). TLR2 exerts downstream effects on myd88. Recently it was shown that TLR2 is essential for microbiota-induced down-regulation of myd88 transcription (Koch et al., Nature Comm 2018, 9:4099). The latter being associated with control of inflammatory signalling. Therefore, commensal bacteria in general such as lactic acid bacteria, and BLPs in particular, may constitute suitable tolerogenic compounds. BLPs are obtained by the acidic heat treatment of *L. lactis* bacteria or any other Gram-positive bacterium, resulting in non-living bacterial particles that predominantly consist of a peptidoglycan surface and lack recombinant DNA. The preparation of BLPs is disclosed in WO 02/101026. The antigenic polypeptides of the present invention may be simply mixed with BLPs or may be loaded onto the BLPs, which employs the non-covalent coupling technology referred to as, Protan technology, disclosed in WO 02/101026 and WO2012/128628. The resulting antigen-associated BLPs (antigen mixed with or bound to BLPs) constitute part of therapeutic formulations that may be delivered to humans via the mucosal layers of the oral cavity and other parts of the gastro-intestinal tract (e.g. mucoadhesive patch, mucoadhesive gel, capsule, tablet or liquid), without the need for an injection. Preferrably, the therapeutic formulations with BLPs and antigen are delivered to humans via the mucosal layers of the oral cavity using a mucoadhesive patch, film or hydrogel. Even more preferably, the therapeutic formulations with BLPs and antigen contain additional tolerizing compounds known in the art such as cytotoxic T lymphocyte antigen 4-immunoglobulin G (Maazi et al. 2013, Clin Exp Immunol 172:113-120), zebularine (WO2008/147283), retinoic acid (Coombes et al. 2007, J Exp Med 204:1757-1764), rapamycin (Maldonado and von Adrian 2010, Adv Immunol 108:111-165), vitamin D3 (Taher et al. 2008, J Immunol 180: 5211-5221) and/or D-mannose (Zhang et al. 2017, Nature Med 23:1036-1047).

In another embodiment of the invention, tolerogenic compositions containing non-living bacterial particals may be prepared from empty bacterial envelopes, so-called bacterial ghosts (BGs). Antigen containing formulations may be based on BGs derived from the strain *Escherichia coli Nissle* 1917, a safe bacterium used in the probiotic pharmaceutical product Mutaflor® or any other safe Gram-negative bacterium. BGs are produced by controlled heterologous expression of a gene which causes a partial lysis of the cell membrane, as disclosed in WO0053163 and WO2015124717, hereby incorporated by reference. An example of such a lytic gene is the gene E of the bacteriophage PhiX174 which codes for a polypeptide which is inserted into the cell membrane complex of Gram-negative bacteria and when oligomerized leads to the formation of a transmembrane tunnel structure through the inner and outer membrane. The inner diameter of this tunnel structure can be 40 to 200 nm or 500 to 1000 nm depending on the lysis conditions. The cytoplasmic material of the cell is released through this tunnel and leaves behind an empty cell envelope having an intact morphology, which can serve as well as delivery vehicle since the empty cell envelopes can be loaded with antigens (WO0053163, WO0154672, WO2005011713). The antigenic polypeptides of the present invention may be simply mixed with BGs or they may be loaded into the empty cell envelopes or they may be co-expressed with the bacteriophage lysin and anchored to the cell envelopes by techniques known in the art (WO9906567; WO0044878). In addition, BGs can also be prepared from Gram-positive bacteria by using a chimeric E-L lysis gene (U.S. Pat. No. 5,075,223).

BGs are exceptionally suitable as carriers or targeting vehicles for antigens or antigen containing material. Since the BGs only contain the desired antigens, a high degree of loading and thus a high tolerizing efficiency of the antigen can be achieved. Notwithstanding the carrier option for BGs, the tolerizing effect can also be achieved by simply mixing the antigen with the BGs. Overall, bacterial ghosts are a safe tolerizing material since they are non-living bacterial particles that do not contain any longer recombinant DNA (WO03006630, WO2009090093). The resulting antigen-associated BGs (antigen mixed with, loaded into or bound to BGs) constitute part of therapeutic formulations that may be delivered to humans via the mucosal layers of the oral cavity or other parts of the gastro-intestinal tract (e.g. mucoadhesive patch, mucoadhesive gel, capsule, tablet or liquid), without the need for an injection. Preferably, the therapeutic formulations with BGs and antigen are delivered to humans via the mucosal layers of the oral cavity using a mucoadhesive patch, film or hydrogel. Even more preferably, the therapeutic formulations with BGs and antigen contain additional tolerizing compounds known in the art such as cytotoxic T lymphocyte antigen 4-immunoglobulin G (Maazi et al. 2013, Clin Exp Immunol 172:113-120), zebularine (WO2008/147283), retinoic acid (Coombes et al. 2007, J Exp Med 204:1757-1764), rapamycin (Maldonado and von Adrian 2010, Adv Immunol 108:111-165), vitamin D3 (Taher et al. 2008, J Immunol 180: 5211-5221) and/or D-mannose (Zhang et al. 2017, Nature Med 23:1036-1047).

In a further embodiment of the invention, tolerogenic compositions containing non-living bacterial particals may be prepared from chemically sterilized non-recombinant food-grade lactic acid bacterial—or probiotic bacterial cultures. Antigen-containing formulations may be based on non-living particles derived from chemically sterilized food-grade Gram-positive and Gram-negative bacteria such as, but not limited to, *Lactococcus*, *Lactobacillus* or *Escherichia* bacteria. In a preferred embodiment of the invention, chemically sterilized *Lactococcus lactis*, *Lactobacillus rhamnosus* or *Escherichia coli* Nissle 1917 are used. Chemical sterilization of bacteria is known in the art. In a preferred embodiment of the invention, chemical sterilization is achieved by the use of alcohol solutions. Examples of alcohol solutions are ethanol and isopropyl alcohol, particularly solutions between 60% and 90% alcohol (v/v) and 10-40% purified water (v/v), are rapidly antimicrobial against bacteria. A contact time between the bacteria and the alcohol solution of 12 hours or more is preferred in order to achieve complete sterilization.

In another preferred embodiment, chemical sterilization is achieved by the use of betapropiolactone. In the used method, betapropiolactone is preferably added at a final concentration of 0.01%-0.1% (v/v) and more preferably of 0.025%-0.5% (v/v). Betapropiolactone may be added in one or more steps, e.g. in two consecutive steps to the preparation, wherein the two portions are preferably of equal amount, wherein the second portion is added about 15-45 min, e.g. at about 30 min. The addition of betapropiolactone preferably occurs as a liquid. Addition as a vapor or aerosol or in other forms is possible. A preferred aspect of the bacterial sterilization by betapropiolactone is an incubation period for 10-60 min, more preferably for 15-45 min, even more preferably for 25-35 min as described in WO2009090093.

Furthermore, suitable incubation temperatures during the chemical sterilization process are between 2° C. and 55° C., more preferably between 20° C. and 40° C. The alcohols or betapropriolactone are aseptically removed from the inactivated bacterial particles by extensive washing with purified water or pharmaceutically accepted neutral buffers with a pH between 6 and 8, more preferably between pH 6.5 and 7.5. Washing of the bacterial particles is done with at least ten times the incubation volume to efficiently remove the sterilizing agent.

The resulting chemically inactivated bacterial particles are a safe tolerizing material since they are of food-grade origin and non-living. According to the invention the antigen is mixed with the chemically inactivated bacterial particles and constitute part of therapeutic formulations that may be delivered to humans via the mucosal layers of the oral cavity or other parts of the gastro-intestinal tract (e.g. mucoadhesive patch, mucoadhesive gel, capsule, tablet or liquid), without the need for an injection. Preferably, the therapeutic formulations with chemically inactivated bacterial particles and antigen are delivered to humans via the mucosal layers of the oral cavity using a mucoadhesive patch, film or hydrogel. Even more preferably, the therapeutic formulations with chemically inactivated bacterial particles and antigen contain additional tolerizing compounds known in the art such as cytotoxic T lymphocyte antigen 4-immunoglobulin G (Maazi et al. 2013, Clin Exp Immunol 172:113-120), zebularine (WO2008/147283), retinoic acid (Coombes et al. 2007, J Exp Med 204:1757-1764), rapamycin (Maldonado and von Adrian 2010, Adv Immunol 108:111-165), vitamin D3 (Taher et al. 2008, J Immunol 180: 5211-5221) and/or D-mannose (Zhang et al. 2017, Nature Med 23:1036-1047).

Antigens

The sequence encoding the antigen can be obtained from any natural source and/or can be prepared synthetically using well-known DNA synthesis techniques. The sequence encoding the antigen can then (for instance) be incorporated in a suitable expression vector, which is then used to transform or transfect the intended host. The recombinant host cell thus obtained can then be cultured, upon which the isolated antigen can be used to formulate the therapeutic composition, optionally after further purification and/or processing steps, such as freeze-drying to form a powder. Optionally, the recombinant host cell bacteria is used to produce BGs, in which case the antigen constitutes part of the BGs and protein purification steps are not required, but instead the BGs containing the antigen of interest are used directly to formulate the therapeutic composition. Antigens can also be produced using well-known protein chemistry techniques. Furthermore, antigens can be obtained as whole intact antigens or partial antigens from extracts, such as pollen, gluten, house dust mite, cat saliva, birch or peanut.

An antigen can be any antigen known to the person skilled in the art. An antigen as used here throughout the application is preferably any substance that provokes an immune response when introduced in the body of an animal, wherein said immune response can be T-cell mediated and/or a B-cell mediated response. The antigen may comprise a T-cell epitope and/or a B-cell epitope. The length of the antigen is not particularly limiting, provided said antigen can be produced. In a preferred embodiment of the invention, the antigen is a whole intact antigen. The antigen can be a protein or a part thereof, such as a polypeptide or a peptide.

The antigens according to the invention include linear and/or conformational epitopes. T-cell mediated responses cover Th1, Th2 and/or Th17 responses. The antigen can be any antigen, such as, but not limited to allergens (including food allergens), allo-antigens, self-antigens, auto-antigens, and therapeutic molecules or antigens that induce an immune response. Preferably, said antigen is involved in the induction of immune response related diseases. Even more preferably, said antigen is involved in the induction of allergic rhinitis, allergic asthma, multiple sclerosis, type I diabetes, autoimmune uveitis, autoimmune thyroiditis, autoimmune myasthenia gravis, rheumatoid arthritis, food allergy, celiac disease, pemphigus vulgaris, neuromyelitis optica, graft versus host disease or anti-drug antibody (ADA) development. Examples of antigens as part of the invention include, but are not limited to: gliadin, hordein, Der p 1, Der p 2, Der p 2.1, Fel d1, pINS, GAD65, $InsB_{9-23}$, MBP, Dsg3, aquaporin 4 or IA2. A more extended list of antigens as part of the invention is found in the Table 8.

The inventors observed that the delivery via a mucoadhesive carrier of immunodominant antigens combined with bacterial particles of the invention suppress systemic inflammatory T-cell responses, and that such formulation and delivery of antigens are necessary and sufficient for the induction of a significant tolerogenic effect.

Regulatory T cells (Treg) play a critical role in the induction and maintenance of oral tolerance. Induction of Treg is a major goal for immunotherapy for several autoimmune, allergic and inflammatory diseases. Current strategies for therapeutic induction of antigen-specific suppressor cells face significant hurdles, and usually require strenuous techniques to isolate, handle and transfer adequate numbers of regulatory cells. The bacterial particle-antigen mucoadhesive carrier delivery system of the present invention circumvents these problems and effectively induces antigen-specific Treg. In the present invention, it was demonstrated that induction of Treg can be achieved by exposing the mucosal immune system to low doses of antigen. The exposure to low doses of antigen is preferably a continued exposure. Hence, the present invention relates to antigens inducing and/or expanding Treg cells, preferably $CD4^+CD25^+$, $CD4^+CD25^-$ and $CD8^+$ Treg cells.

It was further demonstrated in the present invention that the Treg cells which were induced and/or expanded by the antigens according to the invention function through a TGF-β and/or IL-10 dependent mechanism. Previously evidence has been provided that TGF-β plays a critical role in oral tolerance as well as in the development of peripheral induced Treg. Accordingly, the present invention provides immunodominant antigens which stimulate endogenous TGF-β and/or IL-10 expression.

Moreover, it was shown that antigen-specific TGF-β producing Th3 cells drive the differentiation of antigen-specific $Foxp3^+$ regulatory cells in the periphery. Furthermore, TGF-β dependent conversion of peripheral $CD4^+CD25^-$ T cells into $CD25^+$, $CD45RB^{-/low}$ suppressor cells has been reported. It was shown that oral tolerance induced by CTB-conjugated Ag is associated with increase in TGF-β by the generation of both $Foxp3^+CD25^+$ and both $Foxp3^+$ and $Foxp3^-CD25^-CD4^+$ regulatory T cells. These data suggest a key role for $Foxp3^+$ 'adaptive' Treg in the induction and maintenance of oral tolerance. We also show a significant mucosal Foxp3 induction. Moreover, the 'mucosal' induced regulatory T-cell tends to be antigen specific as bacterial particles alone are unable to induce this Foxp3 upregulation within the GALT. Accordingly, the present invention relates preferably to Foxp3+ Treg cells.

The present invention further demonstrated that the Treg cells which were induced and/or expanded by the antigens according to the invention decreased inflammation, in particular in the spleen and secondary lymph node cells. Moreover, the IFN-γ and IL-12 production was decreased. Accordingly, the present invention provides immunodominant antigens which decrease endogenous IFN-γ and/or IL-12 production, and/or stimulate endogenous TGF-β and/or IL-10 expression. Moreover, the present invention relates to antigens reducing proliferation of spleen and/or lymph node cells. It will be appreciated that the present invention relates also to antigens suppressing inflammatory antigen-specific T cell responses.

Immune Response

An immune response related disease as used here is a disease caused by an unwanted immune response of the body against an antigen, whereby said antigen can be either a heterologous antigen or an auto-antigen. Preferably in the methods of the invention for inducing immune tolerance to an antigen, the antigen causes or is associated with an immune response related disease. Immune response related diseases include, but are not limited to allergic reaction including food allergy, celiac disease, allergic asthma, allergic rhinitis, allergic conjunctivitis, atopic dermatitis, autoimmune uveitis, autoimmune thyroiditis, autoimmune myasthenia gravis, rheumatoid arthritis, type I diabetes, pemphigus vulgaris and multiple sclerosis. Immune response related diseases also include unwanted immune reactions such as graft versus host disease or immune activation of medication such as the antibody production against non endogenous Factor VIII. Preferably, the disease is selected from the group consisting of allergic rhinitis, allergic asthma, food allergy, celiac disease, type I diabetes and immune inactivation of therapeutics.

In one embodiment, the invention pertains to a mucoadhesive carrier comprising a non-living bacterial particle and an antigen as herein defined for use in the prevention and/or treatment of an immune response related disease as herein defined, wherein the mucoadhesive carrier is mucosally administered to the subject as herein defined, and wherein preferably, the antigen causes or is associated with the immune response related disease.

According to the present invention the term "immunodominant" relates to the principle of antigens, including peptide fragments and specific epitopes thereof, inducing an immune response.

In view of the above, it will thus be appreciated that the present invention relates to method or use as described herein, wherein said method or use is therapeutic and/or prophylactic.

A further aspect of the invention relates to a method for inducing immune tolerance to an antigen, including peptide fragments and specific epitopes thereof, comprising oromucosal administration of said antigen in combination with bacterial particles in a mucoadhesive patch, film or hydrogel. The antigen may be produced by the micro-organism that is used to make the bacterial particles. In a preferred embodiment of the invention, the purified antigen is produced from another source and mixed with the bacterial particles. The antigen may be physically attached to the tolerizing bacterial particle compound, but the mixed mode can also be without physical interaction of the bacterial particles and the antigen.

Medicament and Administration

Compound means any chemical or biological compound or complex, including simple or complex organic and inorganic molecules, peptides, peptido-mimetics, proteins, protein complexes, antibodies, carbohydrates, nucleic acids or derivatives thereof. An immune-modulating compound is a compound that modifies the function of the immune system. An immune-modulating compound as used here is a tolerance inducing compound; tolerance induction can be obtained, as a non-limiting example, in a direct way by inducing regulatory T-cells such as Treg, Tr1 or Th3, or by shifting the Th1/Th2 balance towards Th1 or Th2, or by inhibiting Th17, or in an indirect way, by activation of immature dendritic cells to tolerizing dendritic cells and/or inhibiting Th2 immune response inducing expression of "co-stimulation" factors on mature dendritic cells. Immune-modulating and immune-suppressing compounds are known to the person skilled in the art and include, but are not limited to organic molecule such as vitamin D3 (or its precursors), D-mannose zebuline, retinoic acid and phosphatidylserine, bacterial metabolites such as spergualin, fungal and streptomycal metabolites such as tacrolimus, rapamicin or ciclosporin, immune-suppressing cytokines such as IL-4, IL-10, IFNα, TGFβ (as selective adjuvant for regulatory T-cells), Flt3L, TSLP and Rank-L (as selective tolerogenic DC inducers), antibodies and/or antagonist such as anti-CD40L, anti-CD25, anti-CD20, anti-IgE, anti-CD3, anti-IL-6 (or IL6R) and proteins, peptides or fusion proteins such as the CTL-4 Ig or CTLA-4 agonist fusion protein.

Delivery or Administration as used here means any method of delivery or administration via mucoadhesive materials known to the person skilled in the art and includes, but is not limited to patches, biofilms or hydrogels comprising or carrying the antigens or bacterial particles combined with the antigens, optionally in presence of compounds such as Vitamine D3 and/or D-mannose that may further enhance the tolerogenic effect and/or penetration enhancers such as surface active components or chelating agents that may enhance oromucosal administration and/or mucosal uptake.

Hydrogels or films as used here mean water swellable, cross-linked polymers that can be impregnated or loaded with antigens and bacterial particles. The bacterial particle-antigen combination loaded into the hydrogel is released in a controlled manner as the hydrogel becomes hydrated within the oral cavity. In a preferred embodiment, the hydrogel matrix in the present invention is comprised of polysaccharides such as chitosan, alginate, and hyaluronic acid. In a more preferred embodiment of the invention the hydrogel matrix is composed of chitosan. Chitosan is a bioactive, biocompatible, biodegradable non-toxic compound with favourable properties for a range of industrial and biomedical applications, including drug delivery, wound healing and biomedical implants. Chitosan is a polysaccharide comprising 1-4-linked residues of 2-mino-2-deoxy-beta-D-glucose (glucosamine) and 2-acetamido-2-deoxy-beta-D-glucose (N-acetylglucosamine). Chitosan is prepared by at least partial deacetylation of the naturally occurring polysaccharide chitin (poly-N-acetylglucosamine or (1→4)-2-deoxy-beta-D-glucan), which is found naturally in the shells of crustaceans, insects and fungi. Thus acetyl groups are removed from at least some of the N-acetylglucosamine residues of chitin to form glucosamine residues.

In commercial preparations of chitosan, usually from about 50% to about 100% of the N-acetylglucosamine residues of chitin have been deacetylated to glucosamine residues. In the present invention chitosan with a deacetylation percentage of 70% to 95% is preferred. Chitosan dissolves to a significant extent in acidic solution, values below pH 6.5. Thus, soluble chitosan is cationic, allowing it to bind to negatively charged surfaces and biological materials. Chitosan is a prominent example of a polysaccharide that can be crosslinked ionically. Chitosan hydrogels can be physically mixed into stable networks by introducing anionic ions or macromolecules to neutralize the positively charged chitosan and induce electrostatic attraction within the gelatinized network. Ionic crosslinking is a relatively safe technique to use for fabricating biocompatible hydrogels without toxic catalysts. According to the present invention chitosan-based hydrogels formulated with non-living bacterial particles and antigen can be dried for long-term storage and easy application in the oral cavity.

In another preferred embodiment of the invention a thermosensitive chitosan solution is used. To obtain a thermosensitive hydrogel, a chitosan solution is neutralized with a polyol counterionic monohead salt is used to neutralize the chitosan solution. Under these conditions chitosan remains liquid at or below 25° C. and can be stored for a long time without losing the thermosensitive properties. The system can then have a pH value within a physiologically acceptable neutral range (pH 6.8-7.2) and it is only the temperature of the milieu that determines the liquid or gel state, gel formation being observed upon an increase in temperature. In a preferred embodiment of the invention the polyol counterionic monohead salt is beta-glycerolphospate and gel formation starts at temperature above 32° C. The production and use of thermosensitive chitosan-based hydrogels is well described in literature, such as "Biological Activities and Application of Marine Polysaccharides" (Arguelles-Monal et al., eds).

Mucoadhesive patches as used here mean patches that consists of multiple polymer layers with different functions. In such multi-layer patches, a mucoadhesive layer covers and overlaps a nanoscaffold reservoir layer as described in Masek et al. (2017, J Control Rel 249:183-195). The mucoadhesive layer serves to attach/adhere to the oral mucosa and is optionally covered by a non-adhesive backing layer to prevent diffusion of the medication into the oral cavity. The nanoscaffold reservoir layer is the actual carrier of the medicament and faces the oral mucosa. The manufacturing of this type of mucoadhesive patch that may involve electrospinning of the nanofibers in the reservoir layer is described in detail in WO2016/051159. In a preferred embodiment therefore, the mucoadhesive (e.g. particle) carrier, comprises: a) a nanoscaffold (or matrix) carrying or comprising at least one substance or API (e.g. in the form of particles), and b) a mucoadhesive (layer), wherein the mucoadhesive (layer), on at least a part of its surface, can adhere (to a mucosa) or overlap with the nanoscaffold. The nanoscaffold preferably contains or has pores having the size of from 10 nm to 1,000 µm and/or is a nanofibrous layer of a thickness in the range 0.1 to 1,000 µm; or comprises a layer of biocompatible polymers or a mixture thereof. 3. The mucoadhesive carrier according to this embodiment can be further characterized in that: a) the mucoadhesive layer (at least partially) overlaps the nanoscaffold, an edge of the mucoadhesive layer overlaps an edge of the nanoscaffold and/or the mucoadhesive layer surrounds the nanoscaffold along an edge; or b) it is adapted for application onto a target mucosa, the nanoscaffold faces the mucosa (e.g. in the same direction as the mucoadhesive) and/or part of the mucoadhesive layer overlapping the nanoscaffold is adapted to adhesively fix (adhere) the mucoadhesive carrier to the target mucosa.

In a preferred use of the invention the multi-layers of the mucoadhesive patch are precasted followed by loading of the nanofiber reservoir layer with the bacterial particles and antigens. For this purpose, the bacterial particles and antigens are applied as a solution, colloid or suspension onto the nanoscaffold reservoir layer. Uptake by the reservoir layer occurs by diffusion and absorbtion. Excess liquid can be removed by conventional drying or lyophilisation techniques. Inclusion of cryoprotective agent(s) may be required to adequately protect bacterial particles and antigens.

The terms "treatment", "treating", and the like, as used herein include amelioration or elimination of a developed mental disease or condition once it has been established or alleviation of the characteristic symptoms of such disease or condition. As used herein these terms also encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. It should be clear that mental conditions may be responsible for physical complaints. In this respect, the term "treating" also includes prevention of a physical disease or condition or amelioration or elimination of the developed physical disease or condition once it has been established or alleviation of the characteristic symptoms of such conditions.

As used herein, the term "medicament" also encompasses the terms "drug", "therapeutic", or other terms which are used in the field of medicine to indicate a preparation with therapeutic effect.

It will be appreciated that the antigen present in the invention is delivered in a therapeutically effective amount. As used herein, the term "therapeutically effective amount" is meant to refer to an amount of a compound or composition of the present invention that will elicit a desired therapeutic or prophylactic effect or response when administered according to the desired treatment regimen. It is observed that when the immune-dominant antigen is continuously present, the inflammatory antigen-specific cell response is even reduced further. This reduction is significantly larger compared to administration of the antigen as such, the bacterial particles as such, or the non-continuous presence of the antigen.

Preferably the compound or composition is provided in a unit dosage form, for example a mucoadhesive patch, biofilm or hydrogel is administered to the oral cavity of a subject, e.g. a patient.

The active ingredients may be administered from 1 to 6 times a day, sufficient to exhibit the desired activity. These daily doses can be given as a single dose once daily, or can be given as two or more smaller doses at the same or different times of the day which in total give the specified daily dose. Preferably, the active ingredient is administered once or twice a day. For instance, one dose could be taken in the morning and one later in the day.

In all aspects of the invention, the daily maintenance dose can be given for a period clinically desirable in the patient, for example from 1 day up to several years (e.g. for the mammal's entire remaining life); for example from about (2 or 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Other constituents of the final formulations may include preservatives, inorganic salts, acids, bases, buffers, nutrients, vitamins, or other pharmaceuticals.

The bacterial particles combined with the antigen may be delivered in a dose of at least 0.1 mg to 60 mg (dry weight) per day, preferably between 0.5 and 20 mg per day, most preferably between 1 and 10 mg per day.

The invention further relates to the following numbered embodiments:

1. A mucoadhesive carrier comprising a non-living bacterial particle for use in oral mucosal administration to treat an immune response related disease in a patient, wherein the non-living bacterial particle is combined with at least one antigen causing said immune response, and wherein said immune response related disease is chosen from the group consisting of celiac disease, allergic asthma, allergic rhinitis, allergic conjunctivitis, atopic dermatitis, multiple sclerosis, type I diabetes, autoimmune uveitis, autoimmune thyroiditis, autoimmune myasthenia gravis, rheumatoid arthritis, pemphigus vulgaris or food allergy.

2. A mucoadhesive carrier according to embodiment 1, wherein the carrier is a mucoadhesive patch, biofilm or hydrogel.

3. A mucoadhesive patch according to embodiment 2, wherein said patch comprises electrospun fibers.

4. A mucoadhesive carrier according to any of embodiments 1 to 3, wherein said antigen is a-gliadin or hordein.

5. A mucoadhesive carrier according to any of embodiments 1 to 3, wherein said antigen is one ore more immunodominant epitopes of house dust mite, preferably Der p 2.1.

6. A mucoadhesive carrier according to any of embodiments 1 to 3, wherein said antigen is one ore more immunodominant epitopes of peptides from cat saliva, skin or glands, preferably Fel d1.

7. A mucoadhesive carrier according to any of embodiments 1 to 3, wherein said antigen is one ore more immunodominant epitopes of peptides involved in Type 1 Diabetes, preferably pINS, GAD65, $InsB_{9-23}$ or IA2.

8. A non-living bacterial particle for use in oral mucosal administration to treat an immune response related disease in a patient, wherein the non-living particle is combined with at least one antigen causing said immune response, and wherein said immune response related disease is chosen from the group consisting of celiac disease, allergic asthma, allergic rhinitis, allergic conjunctivitis, atopic dermatitis, multiple sclerosis, type I diabetes, autoimmune uveitis, autoimmune thyroiditis, autoimmune myasthenia gravis, rheumatoid arthritis, pemphigus vulgaris or food allergy.

9. A mucoadhesive carrier according to any of embodiments 1 to 7, or a non-living bacterial particle according to embodiment 8, wherein the non-living bacterial particle is an acidic heat treated Gram-positive bacterium, preferably *L. lactis*.

10. A mucoadhesive carrier according to any of embodiments 1 to 7, or a non-living bacterial particle according to embodiment 8, wherein the non-living bacterial particle is an empty bacterial envelope obtained from lysing a Gram-negative bacterium, preferably *E. coli* Nissle.

11. A mucoadhesive carrier according to any of embodiments 1 to 7, or a non-living bacterial particle according to embodiment 8, wherein the non-living bacterial particle is a chemically sterilized bacterium, preferably *L. lactis*, Lb. *rhamnosus*, or *E. coli* Nissle.

12. A mucoadhesive carrier or non-living bacterial particle according to any of embodiments 1 to 11 for use as a medicament to treat humans and/or animals.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value. All patent and literature references cited in the present specification are hereby incorporated by reference in their entirety.

The present invention is further described by the following examples which should not be construed as limiting the scope of the invention.

EXAMPLES

Example A1: Determination of Loading and In Vitro Release of Bacterial Particles from a Nanoreservoir Layer Introduction The ability to load BLPs efficiently into precasted nanoreservoir layers made of different types of polymeric fibers was tested as well as the in vitro release of BLPs into buffer from these nanoreservoirs after drying.

Materials and Methods

Bacterial particles: BLPs of *Lactococcus lactis* MG1363 were essentially prepared according to WO 02/101026.

Nanoreservoir layer: nanoreservoir layers were prepared by electrospinning using polycaprolactone (PCL, Mw 80,000 g/mol, Sigma Aldrich) or a mixture (1:1) of polycaprolactone and silk fibroin (PSF) polymers. Procedures were as described by Masek et al. (2017, J Control Rel, 249:183-195). In this way PCL and PSF nanoreservoir layers were obtained with an average pore size of approximately 5 µm.

Experimental setup: nanoreservoir layers of 1 $cm^2$ were loaded with 10 µL BLP solution (5 mg/mL BLP stock in demineralized water) by putting the droplet onto the surface of the reservoir layer. The droplet was allowed to be absorbed into the layer and to be dried at the air at room temperature for about 20 min. Dried reservoir layers with BLPs were either inspected by scanning electron microcospy (SEM; Hitachi8010) or were first submerged into 1 mL PBS for 10 min, followed by drying as described above, prior SEM analysis.

Results

Droplets of BLP solution put onto the surface of PCL nanoreservoirs remained essentially on top of the surface and were not absorbed into the nanoreservoir layer. After 20 min of incubation the droplets were removed and the PCL reservoir layers were dried. SEM analysis revealed that despite the apperent hydrophobicity of the PCL polymers, BLPs had been absorbed onto the polymeric fibers and even entered into some pores, albeit to a limited extend. Submerging PCL nanoreservoirs with BLPs in PBS, completely released the BLPs from the nanoreservoirs indicating that the absorbtion of BLPs to PCL nanofibers is reversible under these conditions.

Droplets of BLP solution put onto the surface of PSF nanoreservoirs were aborbed immediately into the nanoreservoir layer. After drying, SEM analysis revealed a dense loading of BLPs onto the PSF fibers with BLPs also having entered into the pores of the reservoir layer. Submerging PSF nanoreservoirs with BLPs in PBS, released >90% of the BLPs from the nanoreservoirs indicating that the absorbtion of BLPs to PSF nanofibers is reversible under these conditions.

Conclusion

Reservoirs layers of PCL and PSF nanofibers can be used for loading and releasing BLPs, the PSF nanoreservoir layers being the most efficient.

Example A2: Determination of Ex Vivo Release and Penetration into Oral Mucosal Tissue from a Mucoadhesive Patch or Hydrogel of Bacterial Particles Combined with Antigens Introduction The ability of the mucoadhesive patches and hydrogels to target and release associated bacterial particles formulated with antigens in real conditions (moistened mucosal tissue surfaces with limited water volumes, typical of viscous mucus layers etc.) was examined by incubation of mucoadhesive films and hydrogels with cryoaltered mucosa having reduced barrier functions at 37° C. The release of bacterial particles formulated with antigen from mucoadhesive patches and hydrogels in separate experiments was investigated by determination of fluorescence signals on cross-sections of adjacent tissues by confocal microscopy.

Materials and Methods

Bacterial particles: BLPs of *Lactococcus lactis* MG1363 and BGs of *Escherichia coli* Nissle 1917 were essentially prepared according to WO 02/101026 and WO 9906567, respectively. *Lactococcus lactis* MG1363, *Lactobacillus rhamnosus* GG and *Escherichia coli* Nissle were grown overnight in GM17, MRS and TB growth media using standard growth conditions for these organisms. After overnight growth, the cultures were harvested and washed with one volume purified water. Chemically inactivated bacterial particles of *Lactococcus lactis* MG1363, *Lactobacillus rhamnosus* GG and *Escherichia coli* Nissle were obtained by incubation of cell harvests of overnight cultures with 70% ethanol for 16-20 h at 20-23° C. After chemical inactivation, the bacterial particle solutions were centrifuged and the particles were washes three times with the same volume as the original culture. After washing of the untreated bacterial cultures (live bacteria) and the chemically inactivated bacterial particles, the bacteria/particles were resuspended in PBS at a concentration of 30 mg/mL and stored at 2-8° C. until use.

Bacterial particles were labeled with fluorescein isothiocyanate (FITC) by incubation of 3 mg bacterial particles with 0.01 g FITC (Sigma) in 0.1 M boric acid, pH 9.0, for 60 min at room temperature in a shaker. After the incubation the bacterial particles were harvested by centrifugation and washes extensively with PBS and finally stored at a concentration of 30 mg/mL at 2-8° C.

Antigen: Intact, LPS-free OVA grade V protein was used as antigen in all experiments (Sigma Aldrich). A stock solution of 1 mg/mL in PBS was prepared. OVA was labelled with Alexa Fluor 647 (ThermoFisher) according to the instructions of the supplier.

Oral mucosal tissue: Sublingual and buccal tissues were removed using surgical instruments immediately after slaughter of the animal. The excised tissues were transferred immediately to the laboratory in PBS buffer and were cut into cube-shaped pieces used for testing. The interval between slaughter of the animal and start of experiment did not exceed 20 min.

Mucoadhesive patch/hydrogel: the mucoadhesive patches and hydrogels were prepared using polycaprolactone—silk fibroin (PSF), polylactide-co-glycolide—polyethylene glycol (PLGA-PEG) polymer or deacytylated chitosan essentially as described in the referenced patents and description above. Prior to the polymerization process of the hydrogels, bacterial particles and OVA were added to the polymer solutions to final concentrations such that the resulting hydrogels contained 0.1 mg labelled bacterial particles and/or 1 µg labelled OVA per 0.5 cm$^2$. To obtain the mucoadhesive patches, the PSF nanoreservoir layer was overlayed with a mucoadhesive layer consisting of Carbopol 934P (Lubrizol Advanced Materials) and hydroxypropyl methylcellulose K4M (HPMC; Colorcon Ltd) in a 2:1 ratio, such that the mucoadhesive layer is overlapping the PSF nanoreservoir layer. The mucoadhesive layer side that is not attached to the nanoreservoir layer was furthermore covered by a non-adhesive backing layer consisting of Eudragit® L100-55 polymer. The procedure to prepare the precasted mucoadhesive PSF patches is as described by Masek et al. (2017, supra).

A mixture of labelled bacterial particles and OVA was loaded into the mucosadhesive PSF patches such that a concentration was obtained of 0.1 mg labelled bacterial particles and/or 1 µg labelled OVA per 0.5 cm$^2$. The composition of each mucoadhesive patch/hydrogel tested is summarized in Table 1.

TABLE 1

Formulated patches and hydrogels used in the study.

| Ingredient* | Muco-adhesive patch or hydrogel | | | | | | | | | | |
|---|---|---|---|---|---|---|---|---|---|---|---|
| | 1 | 2 | 3 | 4 | 5 | 6 | 7 | 8 | 9 | 10 | 11 |
| OVA | − | + | + | + | + | + | + | + | + | + | + |
| BLP | − | − | − | + | − | − | − | − | − | − | − |
| LL live | − | − | − | − | + | − | − | − | − | − | − |
| LL killed | − | − | − | − | − | + | − | − | − | − | − |
| Lbr live | − | − | − | − | − | − | + | − | − | − | − |
| Lbr killed | − | − | − | − | − | − | − | + | − | − | − |
| BG | − | − | − | − | − | − | − | − | + | − | − |
| EcN live | − | − | − | − | − | − | − | − | − | + | − |
| EcN killed | − | − | − | − | − | − | − | − | − | − | + |

*Lactococcus lactis Bacterium-like particles: BLP; Lactococcus lactis live: LL live; Lactococcus lactis chemically inactivated: LL killed; Lactobacillus rhamnosus: Lbr live; Lactobacillus rhamnosus chemically inactivated: Lbr killed; Escherichia coli Nissle Bacterial ghosts: BG; Escherichia coli Nissle live: EcN live; Escherichia coli Nissle chemically inactivated: EcN killed.

Experimental setup: ex-vivo penetration of antigen loaded bacterial particles into adjacent mucosa was tested on freshly excised porcine sublingual or buccal tissues essentially as described by Masek et al. (2017, supra). Nanofibrous mucoadhesive films/patches with fluorescently labelled bacterial particles and/or OVA were applied to mucosa and incubated for 2 h at 37° C. The surface of each mucosa was moistened (flow rate 0.1 mL/min) with PBS during experiments using a linear pump and tubing.

The release of bacterial particles formulated with antigen from mucoadhesive patches and hydrogels was investigated by determination of fluorescence signals on crosssections of adjacent tissues by confocal microscopy (Leica SP2), essentially as described by Masek et al., 2017.

Results

Ex-vivo penetration of bacterial particles formulated with antigen to oral mucosa was tested on freshly excised porcine sublingual and buccal tissues. A given nanofibrous mucoadhesive film/patch with labelled pre-loaded bacterial particles and/or OVA was applied to excised mucosa and incubated for 2 h at 37° C. During the whole experiment, the surface of the mucosa was moistened with PBS buffer to simulate conditions in the oral mucosa. For control purposes, free bacterial particles were applied to excised mucosa. The difference was clearly distinguishable by means of the intensity of colouration at the site of application. Whereas nanofibrous mucoadhesive patches/films and hydrogels maintained their fluorescent antigen loaded bacterial particles in the middle of a mucoadhesive ring during the incubation period, free bacterial particles were washed out from mucosal surface after a short time of the test and did not penetrate into mucosa at all.

The penetration of bacterial particles formulated with OVA into oral mucosa was confirmed by cross-sectioning of adjacent mucosa and observation with confocal microscopy. Freshly excised sublingual and buccal oral mucosa incubated with mucoadhesive patch and hydrogels were tested. The penetration to the epithelium of the oral mucosa was observed in all tested samples containing bacterial particles. The intensity of fluorescence reflects the concentration gradient of bacterial particles diffusing deeper into submucosal tissue. The transport of bacterial particles in epithelium undergoes the paracellular pathway as clearly demonstrated by confocal microscopy in tissue slices.

Conclusion

Mucoadhesive patch and hydrogels prolong the exposure time of bacterial particles formulated with antigens at mucosal tissues and enable more efficient uptake of said particles and antigen by said mucosal tissues.

Example A3: Determination of In Vivo Release and Penetration into Oral Mucosal Tissue and Draining Lymph Nodes from a Mucoadhesive Patch of BLPs Combined with Antigen Introduction The ability of a mucoadhesive patch to target and release associated bacterial particles formulated with antigen in real conditions, in an oral piglet model, was examined by applying PSF mucoadhesive patches preloaded with labelled BLPs and/or OVA onto the sublingual or buccal oral mucosa. The oral mucosa of swine is generally recognized as a very suitable model for this type of studies as the oral mucosal epithelium is non-keratinized and resembles in this way that of humans. The release of bacterial particles formulated with antigen from the mucoadhesive patches was investigated by determination of fluorescence signals by confocal microscopy on cross-sections of adjacent tissues and draining lymph nodes.

Materials and Methods

Bacterial particles: BLPs of Lactococcus lactis MG1363 were essentially prepared according to WO 02/101026. The particles were labelled as described in Example A2.

Antigen: Intact, LPS-free OVA grade V protein was used as antigen as described in Example A2.

Animals: 2-3 months old Landrace-Yorkshire piglets.

Mucoadhesive patch: PSF mucosadhesive patches were prepared as described in Example A2. Patches of about 2 cm$^2$ were used loaded with labelled BLPs and/or OVA with a final concentration of about 0.1 mg BLPs and/or 1 µg labelled OVA per 0.5 cm$^2$. In some patches the penetration enhancer EDTA was included. The composition of each mucoadhesive patch tested is summarized in Table 2.

TABLE 2

Formulated PSF patches used in the study

| | Mucoadhesive patch | | |
|---|---|---|---|
| Ingredient | 1 | 2 | 3 |
| OVA | + | + | + |
| BLP | − | + | + |
| EDTA | − | − | + |

Each type of patch was applied sublingually (anterior or lateral tongue) or buccally.

Experimental setup: piglets were anaesthesized short-term with Zoletil (Virbac) to apply the patches at the indicated sites in the oral cavity. After 3 hours or 24 hours incubation, the animals were anaesthesized and sacrificed by intravenous application of T61. Sublingual and buccal mucosa with the mucoadhesive patch attached and regional draining lymph nodes were excised, frozen and stored at −80° C. The tissues were treated and analysed by confocal microscopy essentially as described by Masek et al., 2017.

Results

Endocytosis of fluorescent BLPs and OVA by antigen presenting cells (APCs) was demonstrated by confocal microscopy of histochemically stained sublingual and buccal tissue sections. BLPs and OVA were internalized by APCs. Free diffusion of OVA was observed but not of BLPs. The uptake by APCs was more pronounced after 24 hours of attachment of the patches to the oral mucosal tissues. There was a slightly better uptake from patches placed at the buccal locations of the oral cavity and/or in patches that contained the penetration enhancer EDTA. APCs with fluorescent BLPs and OVA were also found in draining regional lymph nodes. This result was most pronounced for patches that contained EDTA and were attached to the buccal mucosa.

Conclusion

Mucoadhesive PSF patches enable efficient uptake of BLPs and antigen at the oral mucosal tissues and said particles and antigen drain to the regional lymph nodes. The presence of a penetration enhancer, such as EDTA, further stimulates the uptake.

Example B: Ex Vivo Determination of Bacterial Particle Mediated Antigen Activation of Buccal Derived Antigen Presenting Cells from Autoimmune and Allergic Patients Introduction To establish that extended exposure of formulations of immunodominant antigens combined with bacterial particles target and activate oral mucosal tolerogenic APCs in a superior manner, a human immune disorder relevant ex vivo model was established by using fresh human oral mucosal tissue from celiac disease and cat allergic patients to study binding of antigen loaded bacterial particles to human oral mucosal APCs with standardized protocols.

Materials and Methods

Bacterial particles: bacterial particles of *Lactococcus lactis* MG1363, *Lactobacillus rhamnosus* GG and *Escherichia coli* Nissle 1917 were essentially prepared as described in Example A2. Additional tolerizing compounds: vitamin D3 (Sigma Aldrich) and D-mannose (Sigma Aldrich) were used to stimulate mucosal uptake and enhance mucosal responses. A single stock solutions of vitD3-mannose (VM) was prepared containing 500 µg/mL of each compound.

Standardized ex vivo model for resorption of antigen loaded particles: specimens of oral mucosal tissue from the vestibular region were obtained from celiac disease-, house dust mite—and cat allergic patients undergoing intraoral surgery, specimens of intestinal biopt material were obtained from celiac disease patients or specimens of peripheral blood mononuclear cells (PBMCs) were used. Patients with tumors were excluded, and only clinically noninflamed tissue was collected. Specimens from individuals with a history of celiac disease based on genetical (HLA-DQ2+ and/or HLA-DQ8+) and serological markers (IgA anti-endomysial and/or IgA-tTG) coupled with duodenal histological alterations as assessed by duodenal endoscopy. Specimens from individuals with a history of house dust mite—or cat allergy was confirmed by skin prick test and/or serum specific IgE.

All specimens were obtained with the approval of the local ethics committee and the medical board ethics committee and after informed consent from patients had been obtained.

Antigens: cat recombinant antigen Fel d 1 was provided by ALK-Albello, purified Der p 1 and Der p 2 house dust mite antigens were purchased from Citeq, recombinant Der p 2.1 (amino acids 1-53) house dust mite antigen was obtained as described by Chen et al. (Mol Immunol. 2008, 45:2486-2498), vital wheat gluten (food grade: Glutival) was purchased from Cargill, the Netherlands and deamidated celiac disease antigen Gliadin α1 peptide (amino acid PFPQPELPY), α2 peptide (PQPELPYPQ) and the 33-mer α2 peptide (LQLQPFPQPELPYPQPELPYPQPQLPYPQPQPF) were purchased from Genscript.

Calculation of migrated oLCs: Collected human oral mucosal tissue was placed mucosal side up on a sterile Petri dish and incubated at 37° C. with PBS containing fluorescein isothiocyanate (FITC)—coupled antigen loaded particles or dextran at concentrations ranging from 10 to 1000 mg/mL. For repetitive antigen challenge, 10 mg/mL antigen mixed with bacterial particles was administered on oral mucosal tissue every 6 minutes by removal of previous and application of new antigen solution without washing between. As control conditions, oral mucosal tissue was incubated with PBS alone or cooled to 4° C. before incubation with FITC-coupled antigen loaded particles or dextran to determine unspecific antigen binding. After incubation, oral mucosal tissue was washed with PBS and placed in RPMI 1640 medium (Invitrogen) containing 10% heat-inactivated FCS (Sigma), 1% antibiotics/antimycotics (Invitrogen), and 500 IU/mL GM-CSF (Berlex Laboratories) at 37° C. In a time kinetic, 24 and 36 hours after antigen exposure, cells that migrated out of the tissue were collected and further processed for flow-cytometric analysis. Medium was exchanged, and incubation of the tissue was continued. After 48 hours, migrated cells were finally collected, and resting tissue was further processed and digested to prepare a single cell suspension by trypsin treatment in 0.5% trypsin buffer without $Ca^{2+}$ for 1 hour at 37° C. as described elsewhere. Binding of antigen to oLCs was calculated by setting gates of the major CD1a1 population in FITC fluorescence, which migrated from tissue at 4° C. Specific binding of antigen was calculated by subtracting the percentage of FITC-positive CD1a cells at 48° C. from the percentage of FITC-positive CD1a cells at 37° C.

Oral mucosal Langerhans cells were gated by their CD1a expression and location in the forward scatter/sideward scatter 24, 36, and 48 hours after antigen/dextran exposure. The remaining tissue was treated with trypsin, and resting oLCs were identified by their CD1a expression. Gated cells were counted at each migration time point as well as in the remaining tissue. The percentage of migrated oLCs at each time point was calculated by adding the number of oLCs at the particular time point and previous time points to divide the sum by the total number of oLCs detected.

Proliferation assays: irradiated APCs were prepulsed overnight with antigen mixed with bacterial particles (concentration range $10^4$-$10^7$ particles per well). Optionally, vitamin D3 and D-mannose we added to the mix as well to a final concentration of 5 µg per well. Allogenic T cells were added the following day, and [$^3$H]thymidine was added 2 d later. Plates were harvested after a further 12-16-h incubation, and [$^3$H]thymidine incorporation was counted on a Betaplate Counter (Wallac Turku) as described by Arentz-Hansen et al. (J. Exp. Med. 2000, 191:603-612).

T-cell proliferation assays using PBMCs were performed as described by Seyfert-Margolis et al. (Diabetes 2006, 55:2588-2594). In short, mononuclear cells were enriched on Ficoll-Paque gradients and seeded at a concentration of $1\times10^5$ per well of a culture-grade, flat-bottom, 96-well culture plate in Hybrimax 2897 protein-free media (Sigma). To allow detection of preactivated as well as anergic T-cells, cultures received 10 units/mL recombinant IL-2 with dilutions made in Hybrimax medium. The responses measured in the presence of IL-2 supplements retain an absolute and dose-dependent requirement for antigen. Plates were incubated in standard $CO_2$ incubators for 1 week, adding 1 µCi [$^3$H]thymidine for the last 12 h before automated harvesting and scintillation counting. PBMC cultures were stimulated with test antigens and test antigens-BLP combinations. To compare proliferative responses in different samples, data were normalized as stimulation indexes (cpm antigen-stimulated/cpm unstimulated). A positive response was defined to be >1.5 and greater than the mean stimulation index in antigen-stimulated culture replicates +3 SDs. The background counts, ranging from 500 to 1,200 cpm, were not significantly different from those in antigen-stimulated cultures (P>0.3). For each sample, positive responses were added, deriving a T-cell response score (range 0-15); a score of 4 was set to be a positive response.

Results

The kinetics and uptake of antigen formulated bacterial particle binding to oLCs and their migration were investigated. To address this issue, freshly ex vivo isolated oral mucosal tissue was incubated with antigen with and without bacterial particles at 100 mg/mL for 1 hour and placed in cell culture medium to let the oLCs that had taken up allergen migrate out of the tissue. Additionally Vitamin D3 and D-mannose were added (see Table 2 for a complete overview of all formulations tested).

TABLE 3

Formulations used in the study.

| Ingredient* | 1 | 2 | 3 | 4 | 5 | 6 | 7 | 8 | 9 | 10 | 11 |
|---|---|---|---|---|---|---|---|---|---|---|---|
| Antigen | − | + | + | + | + | + | + | + | + | + | + |
| VM | − | − | + | +/− | +/− | +/− | +/− | +/− | +/− | +/− | +/− |
| BLP | − | − | − | + | − | − | − | − | − | − | − |
| LL live | − | − | − | − | + | − | − | − | − | − | − |
| LL killed | − | − | − | − | − | + | − | − | − | − | − |
| Lbr live | − | − | − | − | − | − | + | − | − | − | − |
| Lbr killed | − | − | − | − | − | − | − | + | − | − | − |
| BG | − | − | − | − | − | − | − | − | + | − | − |
| EcN live | − | − | − | − | − | − | − | − | − | + | − |
| EcN killed | − | − | − | − | − | − | − | − | − | − | + |

*Vitamin D3 + D-mannose: VM; +/−: sample was tested with or without the component; Lactococcus lactis Bacterium-like particles: BLP; Lactococcus lactis live: LL live; Lactococcus lactis chemically inactivated: LL killed; Lactobacillus rhamnosus: Lbr live; Lactobacillus rhamnosus chemically inactivated: Lbr killed; Escherichia coli Nissle Bacterial ghosts: BG; Escherichia coli Nissle live: EcN live; Escherichia coli Nissle chemically inactivated: EcN killed.

Migrated oLCs were analyzed 24, 36, and 48 hours later for antigen binding. It has been shown that LCs display high dextran uptake. Thus, oral mucosal tissue incubated with FITC-dextran was used as a reference for oLCs binding to antigen. In this context, the total percentage of oLCs binding antigen was lower than the percentage of oLCs binding dextran 24 hours and 36 hours after exposure. Interestingly, the percentage of oLCs binding antigen was comparable 24 hours, 36 hours, and 48 hours after exposure, whereas the percentage of oLCs binding dextran was highest 24 hours after exposure and decreased continuously 36 hours and 48 hours after exposure.

Proliferation assays showed clear patient-specific T-cell proliferation in the presence of antigen. The addition of bacterial particles resulted in a significant decrease in T-cell proliferation, indicating a tolerizing effect. While addition of vitamin D3 and D-mannose also decreased T-cell proliferation, the effect was most pronounced when the bacterial particles were combined with vitamin D3 and D-mannose.

Conclusion

We demonstrate that bacterial particles formulated with antigen are more efficiently targeting the uptake of antigens onto tolerogenic oral APCs compared to antigen alone and further enhanced by the addition of vitamin D3 and/or D-mannose. In addition, we demonstrate that bacterial particles formulated with antigen have a tolerizing effect on T-cells, which is further enhanced by the addition of vitamin D3 and/or D-mannose.

Example C1: In Vivo Induction of Antigen-Specific Desensitization and Disease Modifying Effect by Oromucosal Administration of Bacterial Particles Combined with Antigen to Antigen-Sensitized Mice Introduction Having established that bacterial particles can be used to efficiently target the uptake of antigens onto oral APCs and promote tolegenic responses in vitro, these formulations were tested for their antigen-specific desensitization and disease modifying potential in an in vivo sublingual immunotherapy (SLIT) mouse model, similarly as described by Hesse et al. (Allergy 2018, 73:862-874) for a subcutaneous immunotherapy (SCIT) mouse model.

Materials and Methods

Bacterial particles: BLPs of Lactococcus lactis were prepared essentially as described in Example A1. Optionally, the BLPs were formulated with vitamin D3 and/or D-mannose to a final concentration of 10 mg/mL BLPs and 0.1 mg/mL Vitamin D3 and D-mannose.

Antigen: naturally purified Der p1 and 2 in a 50:1 ratio was purchased from Citeq or intact, LPS-free OVA grade V protein (Sigma Aldrich) was used as antigen in all experiments.

Animals: BALB/cByJ mice were purchased from Charles River Laboratories at an age of 6 to 8 weeks and housed in individually ventilated cages (IVC).

Sensitization of mice: all mice received intraperinoneal injections on day 1 and 15 of 5 µg crude extract HDM (Citeq) or 25 µg OVA adsorbed to 2.25 mg Alum (Imject, Pierce) in 100 µL PBS.

SLIT procedure: groups of 8 mice were treated sublingually 5 times/week with either of OVA-BLP (ratio 1:1 or 5:1 or 1:5) or Der p1/2-BLP (ratio 1:1 or 5:1 or 1:5), a max corresponding dose of free OVA (100 µg) or Der p1/2 (100 µg; 50:1) or, a max corresponding dose of free BLP (100 µg), or PBS buffer during a 8-week period (from day 29 until day 82). SLIT was performed by holding mice in the scruff and applying 2×5 µL of the respective treatment under the tongue. Mice were fixed for additional 20 seconds after each dosing to prevent immediate swallowing of the solution. Table 4 summarizes the formulations that were used in the study.

TABLE 4

Formulations used in the study.

| Ingredient* | Formulation | | | | |
|---|---|---|---|---|---|
| | 1 | 2 | 3 | 4 | 5 |
| PBS | + | + | + | + | + |
| OVA or Der p1/2 | − | + | + | + | − |
| VM | − | − | + | − | − |
| BLP | − | − | + | + | + |

*Vitamin D3 + D-mannose: VM; *Lactococcus lactis* Bacterium-like particles: BLP.

Challenge: two weeks post SLIT procedures challenges were performed by intranasal installation of 25 µg HDM or OVA on days 94, 96, 98, by intranasal administration of the antigen dissolved in PBS (total volume 25 µL). Hereafter, airway responsiveness was determined, and bronchoalveolar lavage fluid (BALF), lungs, and blood were collected and stored for analyses.

Ear swelling response (ESR): before and after SCIT treatment, an ear swelling test (EST) was performed to evaluate the early-phase response to HDM to test for allergic sensitization.

Measurement of airway hyperreactivity to methacholine: airway hyperresponsiveness (AHR) was assessed by measuring airway resistance (R in cmH$_2$O.s/mL) and lung compliance (C in mL/H$_2$O) in response to intravenous administration of increasing doses of methacholine (Sigma-Aldrich). The AHR was expressed as the effective dose of methacholine required to induce a R of 3 cmH$_2$O.s/mL (ED3).

Bronchoalveolar lavage fluid (BALF): lungs were lavaged, and cytospin preparations were made according to Hesse and Nawijn, Inflammation: Methods and Protocols (2017, New York, NY: Springer New York; 2017: 137-168).

T-cell responses: restimulation of lung cells Lung single cell suspensions (5×10$^5$/well) were stimulated for 5 days in RPMI1640 with 0 or 10 µg of DerP1/2 per well, and supernatant was stored in triplo (−80° C.). ELISA determined the concentrations of IL-5, IL-10, IL-13 and IFN-γ, according to the manufacturer's instructions (BD Pharmingen).

Analysis of cytokine levels in lung tissue: the right superior lobe was used for measurement of total protein, and concentrations of IL-4, IL-5, IL-10, IL-13, IL-17, IL-33, IFN-γ, TGF-β, eotaxin/CCL11, TARC/CCL17, and MIP3-α/CCL20 were measured using a MILLIPLEX Map Kit (Merck Millipore) and analyzed according to the manufacturer's protocol.

Antigen-specific Immunoglobulins: blood was collected at several time points in the experiment (pre- and postserum). Mouse sera were analyzed for House dust mite (HDM)-spIgE, Der p1-spIgE and p2-spIgE, Der p1-spIgG1 and Der p1-spIgG2a levels or for OVA-spIgE, OVA spIgG1 and OVA-spIgG2a by ELISA Briefly, polystyrene, high-binding, 96-well flat-bottomed plates (Immulon 2HB; VWR International) were coated with 100 µL/well of antigen (100 µg/mL) in 0.05 M carbonate bicarbonate buffer (pH 9.6) by incubating overnight at 4° C. The plates were washed 3 times (Automatic plate washer, ELX405; BioTek Instruments Inc.) with 200 µL/well of PBS containing 0.5% Tween 20 (PBST), prior to blocking the wells with 200 µL/well of 3% Tween in PBS for 1.5 h at room temperature. Plates were washed 3 times with PBST and sera diluted to 1:100 in PBST were added in triplicates at 100 µL/well and incubated at room temperature for 2 h. Following washing 3 times with PBST, 100 µL of alkaline phosphatase-conjugated secondary antibodies (whole molecule; Sigma) diluted to 1:8,000 was added to the plates and incubated for 1 h at room temperature. Plates were washed and a solution of polynitrophenol-phosphatase substrate (Sigma; 1 mg/mL; 100 µL/well) in diethanolamine buffer, pH 9.8, was added and incubated in the dark at room temperature. Controls included wells without serum and with positive (pooled day 35 sera that had high antibody) and negative sera (pooled sera from day 10). Optical densities (OD) of wells were measured at 405 nm using an ELISA plate reader (EL808; BioTek Instruments Inc.) when the OD of the positive control reached 1. The net absorbance value was calculated for all samples by the instrument software to correct for nonspecific binding effects by subtracting the blank absorbance value from the absorbance value for the well receiving antigen (without serum). The mean OD of each triplicate test serum was expressed as a percentage (percentage positivity) of the positive control as follows: % change OD=[sample OD/(positive control OD−negative control OD)].

Statistical analyses: all data are expressed as mean+/− SEM. The Mann-Whitney U test was used to analyze the results, and $P<0.05$ was considered significant. Within the AHR measurements, a generalized estimated equation (GEE) analysis was used, using SPSS Statistics 20.0.0.2.

Results

Having established that bacterial particles can be used to efficiently target the antigen onto oral APCs and that they have a tolerizing effect on patient-specific T cells, these formulations were tested in pre-clinical SLIT models relying upon OVA- or HDM-sensitized mice. Such mice exhibit severe AHR, lung inflammation associated with cellular infiltrates and systemic OVA- or HDM-specific Th2 immune responses. Ovalbumin- or house dust mite-sensitized mice were sublingually treated 5 days a week for 8 weeks with either PBS, OVA or Der p1/2 alone, BLPs alone or BLP-formulated OVA or Der p1/2. The latter either in the presence of vitamin D3 and D-mannose or not. Sublingual treatment with OVA-BLPs or Der p1/2-BLPs reduced AHR and eosinophilic inflammation in all animals tested and this was most pronounced when a 1:1 ratio was used for antigen: BLP. In addition, a tendency towards a more pronounced AHR and eosinophilic inflammation was observed when vitamin D3 and D-mannose was present in the formulations. In contrast, treatment with soluble OVA or Der p1/2 alone had only a moderate effect on AHR. This ranking was paralleled in the cytokine readouts from animals treated with OVA-BLP or Der p1/2-BLP exhibited marked suppression of type 2 cytokine levels in lung and BALF, and increased antigen-spIgG responses. The levels of antigen-specific IgG1 after SLIT were negatively correlated to levels of IL-5, IL-13, and CCL20 after challenge, indicating a protective role for this neutralizing antibody response in this mouse model. In addition, a higher IL10 and TGF-β production was found in response to the antigen when compared with animals treated with PBS or particles alone indicating the induction of a combined immune shift and regulatory tolerogenic response.

Conclusions

Successful HDM-BLP and OVA-BLP SLIT shifted the Th2 response in lung tissue and BAL fluid towards a more protective Th1/T-regulatory profile that suppresses allergen-specific responses via the production of IL-10 and TGF-β, which resulted in suppressed AHR and eosinophilic inflammation after challenge.

Example C2: In Vivo Induction of Antigen-Specific Tolerance by Bacterial Particles Combined with Antigen to Antigen-Sensitized Wild-Type Piglets Introduction Having established that bacterial particles can be used to efficiently desensitize antigen-sensitized mice, these formulations delivered in a mucoadhesive patch were tested for their tolerance induction potential in an in vivo piglet food allergy model as its known that the oral mucosal system from this species resembles closely the human counterpart.

Materials and Methods

Bacterial particles: BLPs of *Lactococcus lactis* were prepared essentially as described in Example A1. Optionally, the BLPs were formulated with vitamin D3 and/or D-mannose to a final concentration of 30 mg/mL BLPs and 0.1 mg/mL Vitamin D3 and D-mannose.

Antigen: intact, LPS-free OVA grade V protein or Ovm protein was used as antigen in all experiments (Sigma Aldrich). Stock solutions of 1 mg/mL in PBS was prepared.

Mucoadhesive patch: the mucoadhesive patches containing a PSF nanoreservoir were prepared as described in Example A2. BLPs and OVA or Ovm were added to final concentrations such that the resulting mucoadhesive PSF patches contained 0.1 mg BLPs and/or 5 μg vitD3-mannose and/or 1 μg OVA or Ovm per 0.5 cm². Table 5 summarizes the mucoadhesives patches that were used in the study.

TABLE 5

Mucoadhesive patches used in the study.

| Ingredient* | Mucoadhesive patch | | | | |
| --- | --- | --- | --- | --- | --- |
| | 1 | 2 | 3 | 4 | 5 |
| OVA or Ovm | − | + | + | + | − |
| VM | − | − | + | − | − |
| BLP | − | − | + | + | + |

*Vitamin D3 + D-mannose: VM; *Lactococcus lactis* Bacterium-like particles: BLP.

Sensitization of pigs: outbred litters of naïve Landrace-Yorkshire piglets were used in a split-litter design for induction of OVA or Ovm hypersensitivity according to the protocol described by Rupa et al. (Int Arch Allergy Immunol. 2008, 146:11-18) and Rupa et al. (Vet Immunol Immunopathol. 2011, 140:23-29). Pigs were bled at 10 days of age via the retro-orbital sinus to obtain pre-sensitization sera and were randomly assigned to 4 treatment groups (n=6/group). Three groups received intraperitoneal injection of 100 or 200 μg OVA or 100 μg Ovm with various doses (10, 25 or 50 μg) of cholera toxin (CT; List Biological Laboratories Inc.) in 200 μL of phosphate-buffered saline (PBS; 0.1 M, pH 7.4) administered on days 14, 21 and 35. The fourth group (control) received 50 μg of CT alone. Blood was collected for serum on days 21, 35 and 45 to detect progression in immune response. After coagulation for 1 h at room temperature, individual sera were collected and stored at −20° C. for detection of IgG (whole molecule)-related antibodies to OVA or Ovm. Equal amounts of individual sera of littermates were pooled (sensitized and controls pooled separately) for PCA reaction. On day 45, 52, 59, 66, 73, 80 the animals were treated with an oromucosal PSF patch applied at the sublingual or buccal oral epithelium. Pigs were monitored for clinical signs of allergy after the challenge (0-60 min).

Challenge: on day 92 the animals received an oral challenge with 40 mL of yoghurt slurry comprising 3:2 (v/v) eggwhite:yoghurt.

Sera analysis:_pig sera were analyzed for anti-OVA or anti-Ovm antibodies by ELISA. Briefly, polystyrene, high-binding, 96-well flat-bottomed plates (Immulon 2HB; VWR International) were coated with 100 μL/well of OVA or Ovm (100 μg/mL) in 0.05 M carbonate bicarbonate buffer (pH 9.6) by incubating overnight at 4° C. The plates were washed 3 times (Automatic plate washer, ELX405; BioTek Instruments Inc.) with 200 μL/well of PBS containing 0.5% Tween 20 (PBST), prior to blocking the wells with 200 μL/well of 3% Tween in PBS for 1.5 h at room temperature. Plates were washed 3 times with PBST and sera diluted to 1:100 in PBST were added in triplicates at 100 μL/well and incubated at room temperature for 2 h. Following washing 3 times with PBST, 100 μL of alkaline phosphatase-conjugated rabbit anti-pig IgG (whole molecule; Sigma) diluted to 1:8,000 was added to the plates and incubated for 1 h at room temperature. Plates were washed and a solution of polynitrophenol-phosphatase substrate (Sigma; 1 mg/mL; 100 μL/well) in diethanolamine buffer, pH 9.8, was added and incubated in the dark at room temperature. Controls included wells without serum and with positive (pooled day 35 sera that had high antibody) and negative sera (pooled sera from day 10). Optical densities (OD) of wells were measured at 405 nm using an ELISA plate reader (EL808; BioTek Instruments Inc.) when the OD of the positive control reached 1. The net absorbance value was calculated for all samples by the instrument software to correct for nonspecific binding effects by subtracting the blank absorbance (without serum) value from the absorbance value for the well receiving OVA or Ovm antigen. The mean OD of each triplicate test serum was expressed as a percentage (percentage positivity) of the positive control as follows: % change OD=[sample OD/(positive control OD−negative control OD)].

Cutaneous Hypersensitivity; intradermal skin tests were performed in all animals, prior to sensitization on day 10 and after sensitization on days 21, 35, 46, 67 and 88 to test for immediate active hypersensitivity reactions. Injection sites on the inner thighs were marked with an indelible ink pen. For each skin test, 100 μL (100 μg) of OVA or Ovm in PBS was injected intradermally using a tuberculin syringe and 25-gauge needle. The negative control was PBS. All intradermal tests (serum and PBS) were performed and read at the same time. One investigator performed all injections. Each site was examined individually by at least 2 observers for wheal and flare response 15 min after injection and consensus was reached regarding positivity or negativity.

Clinical Scores: hypersensitivity responses were evaluated using a scoring system after induction by oromucosal challenge on day 92. The response was scored visually by at least 3 observers in a blinded fashion 0-60 min after oral challenge. Each pig was individually assessed and scored as follows: 0=no signs; 1=immobility, lethargy, malaise, scratching, rash; 2=diarrhea, emesis; 3=increased respiratory rate, neck extension; 4=forced expiration; 5=other signs (various). Total scores were obtained by adding individual scores assigned to each animal.

Passive Cutaneous Anaphylaxis: sera were pooled from treatment groups (CT-treated controls and sensitized) and aliquots were treated by heating at 56° C. for 4 h to inactivate putative IgE-anti-OVA or anti-Ovm PCA-mediating antibodies. Sera were injected intradermally in duplicate 100 μL volumes into marked sites on the inner thighs of naïve pigs. After 24 h, 5 mg of OVA or Ovm in 1.0 mL of sterile PBS was injected via a dorsal ear vein using a 23-gauge needle. Cutaneous injection sites were examined by at least 3 observers for expression of a wheal and flare reaction. Sera obtained from sensitized pigs in each of the litters were also tested individually for PCA response and each site was graded (+, ++, +++, ++++) on the basis of relative severity.

Analysis: data were analyzed using InStat Package 4.0 (GraphPad Software Inc.). The confidence interval was set to be at least 95% in assessing significance. Comparisons were made between day 10 versus day 45 serum IgG-anti-OVA or anti-Ovm and control (CT) versus sensitized (OVA or Ovm) antibody. The primary data for comparisons of antibodies detected were analyzed with a one-way ANOVA test using animal as the experimental unit followed by Tukey's multiple comparison test for significant differences between treatment groups. The relationship between PCA reaction and clinical score was evaluated by linear regression and Pearson correlation analysis (GraphPad Prism, version 4.0).

Results

Having established that bacterial particles can be used to efficiently target the antigen onto oral APCs and that they have a tolerizing effect on patient-specific T cells, these formulations were tested in a pre-clinical model relying upon OVA- or Ovm-sensitized piglets. Such piglets exhibit severe AHR, lung inflammation associated with cellular infiltrates and systemic OVA- or Ovm-specific Th2 immune responses. Ovalbumin- or Ovomucoid-sensitized piglets were oromucosally treated once weekly for 6 weeks with either PBS, OVA or Ovm, BLPs alone or BLP-formulated OVA or Ovm delivered via a mucoadhesive PSF patch.

Oromucosal treatment with OVA or Ovm loaded BLPs administered with a mucoadhesive PSF patch dramatically reduced AHR in all animals tested, whereas treatment with soluble OVA or Ovm alone had only a moderate effect on AHR and OVA or Ovm loaded BLPs had intermediate effects as measured by cell responses were assessed in mediastinal and cervical LNs recovered from piglets after a 6-week oromucosal regimen. This ranking was paralleled in the cytokine readouts from cervical LNs from animals treated with mucoadhesive OVA-BLP or Ovm-BLP exhibited lower IL-13 and IL-5 production and higher IL10 production in response to the antigen when compared with animals treated with PBS or particles alone indicating the induction of a combined immune shift and regulatory tolerogenic response.

Conclusions

We demonstrate that oral mucosal delivery of an antigen by a BLP-mucoadhesive PSF patch is superior in directing immune responses towards a short course regulatory and tolerance inducing effect compared to antigen alone in a human-like food allergy model. In addition, the presence of vitamin D3 and D-mannose further enhances the tolerogenic effects.

Example D1: Induction of Tolerance to Insulin Following Oromucosal Administration of BLP Combined with Said Autoantigen Introduction Autoimmunity is characterized by spontaneous inflammatory tissue damage and by impaired physiological function resulting from loss of tolerance to self-antigen. It is associated with a partially overactive immune system, which is characterized by an excess of T helper (Th) cells. Predisposing factors, such as susceptibility genes and environmental factors are difficult to influence, therefore recent efforts to develop immunotherapies are focused on re-establishing the functional balance between pathogenic effector cells and immunoregulatory T cells by depleting the former and/or enhancing the latter. Autoimmune destruction of pancreatic islet beta cells is the major cause of Type 1 diabetes mellitus (T1D). This destruction is associated with cellular and humoral immune responses to several beta cell autoantigens, both of which can precede the clinical onset of disease.

Here, we demonstrate that oromucosal delivery of an autoantigen combined with bacterial particles suppresses diabetic-specific immune responses via the induction of antigen-specific CD4$^+$ regulatory T cells.

Material and Methods

Bacterial particles: BLPs of *Lactococcus lactis* were prepared essentially as described in Example A1. The BLPs were formulated with vitamin D3 (Sigma Aldrich) and D-mannose (Sigma Aldrich) to a final concentration of 10 mg/mL BLPs and 0.1 mg/mL vitamin D3 and D-mannose, and/or 10 mg/mL antigen. Table 6 summarizes the formulations used.

Antigen: the insulin peptide fragment InsB$_{9-23}$.

TABLE 6

Formulations used in the study.

| Ingredient* | Formulations | | | | |
|---|---|---|---|---|---|
| | 1 | 2 | 3 | 4 | 5 |
| PBS | + | + | + | + | + |
| Antigen | − | + | + | + | − |
| VM | − | − | + | − | − |
| BLP | − | − | + | + | + |

*Vitamin D3 + D-mannose: VM; *Lactococcus lactis* Bacterium-like particles: BLP.

Mice

Non-obese female and male diabetic (NOD) mice and NOD-severe combined immunodeficient (SCID) (Balb/c background) mice were purchased from the Jackson laboratory. Balb/c wild type (WT) mice were purchased from Charles River Italy. Mice were maintained in a specific pathogen-free central animal facility. Mice were treated and used in agreement with the institutional guidelines.

Experimental Setting

In a therapeutic setting the BLP-InsB$_{9-23}$ combination (or BLP as a control) was administered sublingually to diabetic NOD mice 5 times a week for 8 consecutive weeks. The mice were sacrificed 1 week after finalization of the SLIT procedure and analyses were performed.

SLIT procedure: groups of 8 NOD female mice showing stable glycosuria and hyperglycemia (12-23 weeks) were treated sublingually 5 times/week with either of BLP-InsB9-23 solution (100 µg BLP and 100 µg InsB9-23 per dose) or BLP (100 µg) and PBS controls. SLIT was performed by holding mice in the scruff and applying 2×5 µL of the respective treatment under the tongue. Mice were fixed for additional 20 seconds after each dosing to prevent immediate swallowing of the solution. For the positive (tolerizing) control group, diabetic NOD mice were treated as described in Bresson et al. (J. Clin Invest. 2006, 116:1371-1381). Complete remission was defined as the disappearance of glycosuria and a return to normal glycemia.

In a syngeneic islet transplantation setting, female NOD mice with recent-onset diabetes were treated sublingually 4 weeks with BLP-InsB$_{9-23}$, or with BLP as a negative control. After 4 weeks, 500 freshly isolated pancreatic islets from non-diabetic NOD mice were transplanted to diabetic NOD mice. Blood glucose was then monitored 3 times weekly until diabetes recurrence or until 15 weeks after grafting. Animals with 2 consecutive glucose levels ≥250 mg/dL were considered diabetic and will be subsequently killed for serum collection and histological analysis of the graft.

The precise mechanisms of tolerance induction were analyzed in vitro and in vivo after re-challenging the NOD mice with specific autoantigens and by adoptive T-cell transfer into NOD-SCID mice.

Detection of Diabetes:

Glucose monitoring: urine glucose was measured by using Diastix (Miles) and was confirmed by blood glucose measurements with the blood glucose monitoring system OneTouch Ultra (LifeScan Inc.). Diabetes was defined as 2 consecutive blood glucose values superior to 250 mg/d L.

Insulitis: Mice were killed by $CO_2$ asphyxiation and the pancreas was fixed in 10% formalin overnight, embedded in paraffin, and serial 5 µm sections were stained with haematoxylin and eosin. The insulitis score (mean±SD) was determined by microscopically grading the degree of cellular infiltration in 10-15 islets/mouse as follows: 0, no visible sign of islet infiltration; 1, peri-islet infiltration; 2, <50% infiltration; 3, >50% infiltration.

Islet isolation and transplantation: Islets of insulitis- and diabetes-free 14- to 21-day old donor NOD mice were isolated after aseptic removal by digesting the pancreatic glands with collagenase in Hanks' balanced salt solution during vigorous shaking. Islet isolation was carried out by direct hand-picking under a stereo-microscope. Diabetic recipient NOD mice were anaesthetized by intraperitoneal injection of avertin (0.02 mL/g BWT), the left kidney was exposed via lumbar incision and 500 freshly isolated islets were given under the renal capsule.

Immunohistochemistry

To detect insulin, CD4 and CD8 expression in pancreatic ß cells, primary Abs (guinea pig anti-swine insulin from Dako [dilution 1:300], anti-CD4 RM4.5 and anti-CD8a IHC from BD Biosciences [dilution 1:50] were applied to frozen tissue sections as described in Christen et al. (Diabetes 2004, 53:591-596).

In Vitro Proliferation Assay

Single cell suspensions of spleen, mesenteric LN (MLNs) and PLNs are prepared. Proliferation assays of total splenocyte populations, 2×10$^5$ cells were cultured in 96-well U-bottom plates in a total volume of 200 µL complete medium either alone or with graded concentrations (1-100 µg/mL) of purified human insulin or peptides specific for CD4 T cells (InsB$_{9-23}$, H-2$^{d\ or\ g}$ restricted) or for CD8 T cells (InsB$_{15-23}$, K$^d$ restricted) (Sigma), and either with or without anti-IL-10 or anti-TGF-β neutralising monoclonal antibodies. The neutralizing antibodies were added at 1, 0.1 and 0.01 µg/mL. For proliferation assays of total CD3$^+$ T cells, CD8$^+$ T cells, CD4$^+$ T cells and CD4$^+$CD25$^-$ T-cell populations, 0.2×10$^5$ cells T cells were cultured in 96-well U-bottom plates with 1×10$^5$ irradiated splenocytes from WT Balb/c mice loaded with insulin or GAD65 or peptides specific for CD4$^+$ or CD8$^+$ T cells, in a total volume of 200 µL complete medium either with or without neutralizing antibodies. After 72 hr at 37° C. in a 5% $CO_2$ humidified incubator, proliferation was assessed by addition of 1 µCi/well [$^3$H]-thymidin. DNA-bound radioactivity is harvested 16-18 hr later onto glass fiber filter mats (Perkin Elmer, Boston, USA) and thymidine-incorporation was measured on a scintillation counter (Perkin Elmer). T-cells were purified from PLNs or spleens by negative selection through magnetic bead separation using CD3$^+$, CD4$^+$ or CD8$^+$ isolation kit (MACS; Milteny Biotec, Auburn, CA). CD4$^+$ T cells are used as total cells or further separated into CD25$^+$ and CD25$^-$ by MACS using CD25$^+$ isolation kit (Milteny Biotec). The purity (>90%) of the cell populations is determined by flow cytometric analysis.

For cytokine measurements, supernatants of the cell cultures used in the different proliferation assays (antigen-specific stimulation), described above, were collected after 72 h of culture and frozen at −80° C. until cytokine analysis was performed. Cytokine production is quantified using the Mouse Inflammation Cytometric Bead Assay (BD Biosciences, Mountain View, CA, USA). Purified CD3$^+$ T cells, CD4$^+$ T or CD8$^+$ T cells were cultured and stimulated in vitro non-specifically with an anti-CD3/anti-CD28 mixture (1 µg/mL each) for 24 hours or they remained unstimulated as control. The supernatants were harvested, and analysed for IL-10, IL-4, IL-5 and IFNγ production using BD™ Cytometric Bead Array flex set on a BD FACSArray Bioanalyzer using the FCAP array software (BD Biosciences). Capture ELISA experiments were used to determine TGF-ß1 using the Quantikine kit (R&D Systems).

In Vitro T Cell Proliferation Inhibition Assay

2×10$^4$ purified total splenic CD4$^+$CD25$^-$ T cells isolated from recently diabetic female NOD (8-12 weeks) were co-cultured with varying numbers of CD8$^+$ T cells, CD4$^+$ T cells and CD4$^+$CD25$^-$ T cell populations isolated from the spleen, MLN or PLNs from the different experimental groups in the presence of 2×10$^4$ T-cell depleted irradiated insuline- or peptides-loaded splenocytes from WT Balb/c mice. After 72 hr at 37° C. in a 5% $CO_2$ humidified incubator, proliferation is assessed by addition of 1 µCi/well [$^3$H]-thymidin. DNA-bound radioactivity was harvested 16-18 hr later onto glass fiber filter mats (Perkin Elmer, Boston, USA) and thymidine-incorporation measured on a scintillation counter (Perkin Elmer).

In Vitro Cytotoxicity Assay

Lymphoblast targets used were Con A-activated splenocytes from BALB/c mice. A total of 10$^6$ target cells were labelled with 100 µCi of $^{51}$Cr (Amersham International, Buckinghamshire, UK) for 90 min at 37° C., washed three times and then incubated with 1 µg/ml peptide (InsB$_{15-23}$ or an irrelevant peptide) at 37° C. for 1 h. Target cells were washed two times and seeded at 10$^4$ cells per well. CD8$^+$ T cells, isolated from spleen, MLNs and PLNs were added to each well, in triplicate, at various effector:target (E:T) ratios. The plates were centrifuged at 500 rpm for 2 min, and incubated at 37° C. for 4 h. After incubation, supernatants were collected for determination of $^{51}Cr$ release [% lysis=100×(test cpm−spontaneous cpm)/(total cpm−spontaneous cpm)]. For the indirect killing assay, $CD8^+$ T cells were incubated with 5 µg/mL anti-CD3 antibody (clone 145-2C11, Pharmingen) prior to incubation with effectors.

Adoptive Transfer of Diabetes

NOD-SCID mice at 8-10 wk were injected intraveneously with $2\times10^7$ or intraperitonally with $5\times10^6$ splenocytes isolated from diabetic female NOD mice (6 weeks, 12 weeks and 18 weeks) combined with or without graded numbers of bead-purified $CD3^+$ T cells, $CD8^+$ T cells, $CD4^+$ T cells, $CD4^+CD25^-$ or $CD4^+CD25^+$ T cells isolated from the different experimental BLP-treated groups. Untreated mice were used as control. Development of diabetes was determined by continuous monitoring of blood glucose levels three times a week.

Results

BLP-$InsB_{9-23}$ delays diabetes recurrence after syngeneic islet transplantation. To assess whether BLP-InsB(9-23) induce oral tolerance, diabetes recurrence after syngeneic islet transplantation was studied. Therefore, mice were oromucosally treated as described above (experimental setting) and pancreatic islets were transplanted as described (Islet isolation and transplantation). Diabetes recurrence was delayed in the $InsB_{9-23}$ group in comparison to the control.

BLP-$InsB_{9-23}$ significantly enhanced the tolerance-inducing capacity of free $InsB_{9-23}$ in the non-obese diabetic mouse. To study the induction of oral tolerance, mice are oromucusally treated as described above (experimental setting). Administration sublingually of BLP-$InsB_{9-23}$ significantly enhanced the tolerance induction towards autoantigen as the autoantigen-specific proliferative response of the splenocytes was significantly reduced in the $InsB_{923}$ group in comparison to the control and free $InsB_{9-23}$ groups.

BLP-$InsB_{9-23}$ potentiated oral tolerance in association with reduced insulitis, deceased rate of beta cell destruction, and increased IL-10 production by splenocytes. To study the induction of oral tolerance, mice were orally fed as described above (experimental setting). The presence of insulitis, the rate of beta-cell destruction and cytokine production in response to said autoantigen was determined as described above. Histological analysis shows a significant lower degree of insulitis and beta cell destruction and increased IL-10 production in the BLP-$InsB_{9-23}$ group in comparison to the control and free-$InsB_{9-23}$ groups.

BLP-$InsB_{9-23}$ enhances oral tolerance via $CD4^+$ T cells. To assess whether CD4 T cells mediate the induction of oral tolerance, the autoantigen-specific proliferative CD4 T-cell response was studied in the splenocytes and lymph nodes. Therefore, mice were orally fed as described above (experimental setting) and the autoantigen-specific $CD4^+$ T cell proliferation is determined as described (in vitro proliferation assay). The autoantigen-specific CD4 T cell response in the BLP-$InsB_{9-23}$ group in comparison to the control and free-$InsB_{9-23}$ groups.

Autoaggressive $CD8^+$ responses are suppressed in NOD mice following BLP-$InsB_{9-23}$ therapy. To examine whether our combination approach induce suppressive CD4+ T cells that are capable of modulating diabetes by bystander suppressive mechanisms, we analyzed the effect on CD8+ autoaggresive T cells. The percentage and/or activity of antigen-specific autoaggressive CD8+ cells was strongly reduced after BLP-$InsB_{9-23}$ therapy.

Antigen-induced T regulatory cells following BLP-$InsB_{9-23}$ therapy can transfer protection from autoimmune-like responses in vivo. In order to test for active suppression of diabetic-like responses in mice treated with the oral tolerance protocol, we adoptively transferred splenocytes from the different treated groups as described above (adoptive transfer of diabetes). Compared with controls and free-$InsB_{9-23}$ group, diabetic-like responses were significantly reduced in the BLP-$InsB_{9-23}$ group, indicating activation of regulatory $CD4^+$ T cells in our combination oral tolerance protocol.

Conclusion

We demonstrate that oral mucosal delivery of an autoantigen by a bacterial particle oromucosally suppresses immune responses in autoimmune diseases via the induction of antigen-specific $CD4^+$ regulatory T cells.

Example D2: Induction of Tolerance to Gliadin Following Oral Administration of BLP Combined with Said Autoantigen Introduction Celiac disease is caused by a loss of tolerance to ingested dietary gliadin and is mediated by HLA-DQ2 or HLA-DQ8 restricted T-cell response. Effective treatment can only be reached by a socially restrictive diet that requires lifelong abstinence from foods that contain gliadin present in wheat or proteins from related cereals like rye or barley. While a strict gluten free diet can lead to healing of the intestine, the intolerance to gluten is permanent and better therapeutic options are needed. For celiac disease the trigger (the gluten protein gliadin), the genetic association (HLA-DQ2 or HLA-DQ8), and the highly specific humoral response have been well characterized. Because disease activity is strongly correlated to the presence and dosage of antigen, the induction of antigen-specific oral tolerance using sublingual delivery of the medicament (SLIT) is an attractive therapeutic approach. Oral tolerance is mediated by multiple mechanisms such as anergy, deletion and/or active suppression of antigen-specific effector T cells by regulatory T cells (Tregs).

Here, we investigate whether oral delivery of a deaminated gliadin peptide in the presence of BLPs induces suppression of systemic DQ8-specific T-cell responses in NOD AB° DQ8 transgenic mice and provides a method for the induction of DQ8d antigen-specific tolerance.

Material and Methods

Bacterial particles: BLPs of *Lactococcus lactis* were prepared essentially as described in Example A1. Optionally, the BLPs were formulated in PBS with vitamin D3 (Sigma Aldrich) and D-mannose (Sigma Aldrich) to a final concentration of 10 mg/mL BLPs and 0.1 mg/mL vitamin D3 and D-mannose, and/or 10 mg/mL antigen.

Antigen: the deaminated DQ8d peptide GAPVPYPDPLEPRQYPSGEGSFQPSQENPQA was purchased from Genscript.

Table 7 summarizes the oral formulations that were used in the study.

TABLE 7

Formulations used in the study.

| Ingredient* | Formulations | | | | |
|---|---|---|---|---|---|
| | 1 | 2 | 3 | 4 | 5 |
| PBS | + | + | + | + | + |
| DQ8 peptide | − | + | + | + | − |
| VM | − | − | + | − | − |
| BLP | − | − | + | + | + |

*Vitamin D3 + D-mannose: VM; *Lactococcus lactis Bacterium*-like particles: BLP.

Mice

NOD AB° DQ8 transgenic and NOD AB° mice were purchased from Mayo Clinic. Seven to sixteen week old mice were used for the experiments. Mice were weaned and maintained on gluten free chow and were kept in a conventional animal facility until 8-12 weeks of age. Mice are treated and used in agreement with the national guidelines.

Experimental Setting

NOD AB° DQ8 mice on a gluten free chow were sensitized by subcutaneous injection of 100 μg DQ8d peptide in 100 μL of a 1:1 CFA (Complete Freund's Adjuvant, purchased from Difco of Becton, Dickinson and Company) saline solution in the tail base at day 1. The peptide used for the sensitization had the same sequence as the peptide used in the treatment. Seven to sixteen week old mice were used for the experiments. Mice were weaned and maintained on gluten free chow and were kept in a conventional animal facility until 8-12 weeks of age. Groups of 8 mice were used per treatment group. Mice received PBS as a negative control, and the formulations as tabulated in Table 7. Mice were treated sublingually 5 times/week with either of 100 μg DQ8d and/or 100 μg BLP per dose or PBS buffer during a 8-week period. SLIT was performed by holding mice in the scruff and applying 2×5 μL of the respective treatment under the tongue. Mice were fixed for additional 20 seconds after each dosing to prevent immediate swallowing of the solution. Antigen-specific DTH responses were assessed 4 times with a weekly interval starting one week after SLIT treatment. Twenty-four hours thereafter, DTH measurements were performed. For measurement of antigen-specific DTH responses, baseline ear-thickness was measured using an engineer's micrometer (Mitutoyo). Mice were then injected with 10 μg DQ8d in 10 μL saline in the auricle of the ear. The ear-thickness was measured again in a blinded fashion at 24 h after challenge. DTH responses were expressed as the difference in the baseline ear-thickness and the ear-thickness 24 hours after DQ8d injection. Subsequently, mice were sacrificed, spleen and lymph nodes were harvested and cells were assessed for DQ8d-specific proliferation and cytokine production.

Isolation of Lamina Propria Cells: mice were euthanized by CO₂ inhalation, and the small intestine removed and cut longitudinally and laterally into 2 cm long pieces using a scalpel blade. The tissue was then washed six times using CMF/HEPES solution (1× Hanks balanced salt solution, 15 mM HEPES, 2% FBS) followed by a one hour incubation in CMF/FBS/EDTA solution (1× Hank's balanced salt solution, 10% FBS, 15 mM HEPES, 5 mM EDTA, 100 μg Penicillin/Streptomycin) to remove epithelial cells. A subsequent collagenase (100 U/mL) digestion was performed for one hour to release the lamina propria lymphocytes.

Cell cultures, proliferation and cytokine production assays: cell suspensions of spleen and lymph nodes were prepared at day 11 of the experiment by homogenizing the tissue with a tissue grinder (VWR International, Inc.) in 1×PBS. Erythrocytes were removed from the spleen cell suspensions by incubation with Ammonium Chloride/Potassium lysis buffer. Cells were incubated in 96-well microtiter plates at 5×10⁵ cells/well in 0.2-mL volumes at 37° C. in RPMI 1640 (1.5% Hepes, 1% Penstrep and 10% FBS) with supplements containing either medium alone, 10 μg/mL Con A, 50 μg/mL irrelevant peptide, or 50 μg/mL DQ8d epitope. In a separate experiment IL-10, TGF-β, IL10& TGF-β or LAP neutralizing antibodies were added to splenocytes of treated mice. After 24 h, proliferation was assessed by addition of 1 μCi/well [³H]-thymidine for the last 24 h of culture. DNA-bound radioactivity was harvested onto glass fiber filter mats (Perkin Elmer) and thymidine-incorporation measured on a scintillation counter (Perkin Elmer). Results were expressed as mean counts per minute (CPM) of triplicate wells. For the neutralizing antibody proliferation assay the results were expressed as the percentage of proliferation in the treatment group compared to the PBS treated group. For cytokine measurements, supernatants of the cell cultures used in the different proliferation assays, described above, were collected after 24 h of culture and frozen at −20° C. until cytokine analysis was performed. Cytokine production was quantified using the Mouse Inflammation Cytometric Bead Assay (BD Biosciences).

T-cell Proliferation Assay Using Lamina Propria Cells: Lamina Propria cells were isolated from SLIT treated. These cells (5×10⁶ cells/mL) were then incubated with medium (RPMI, Sigma-Aldrich), DQ8d epitope (50 μg/mL) or irrelevant peptide (50 μg/mL), for 24 hours before the addition of [³H]-thymidine for an additional 24 hours. Cells were then harvested in a similar fashion as the splenocytes.

Flow cytometric analysis: spleens and cervical lymph node tissue of SLIT treated mice were isolated, prepared as described above and stained for CD4, CD25 and Foxp3. Intracellular staining was performed for Foxp3 according to the manufacturer's instructions (eBiosciences) and subsequently measured using flow cytometry on a Becton Dickinson FACSCaliburs. Cells were gated on CD4⁺CD25⁺ and CD4⁺CD25⁻ subpopulations and within these populations Foxp3 histograms were used to determine Mean Fluorescence Intensity (MFI).

T-cell phenotyping: CD4 and CD25 antibodies were purchased from BD Biosciences, and APC anti-Foxp3 staining kits were purchased from eBiosciences. Anti-IL-10 neutralizing monoclonal antibody (1 μg/mL, clone JES052A5), TGF-β neutralizing monoclonal antibody (1 μg/mL, clone 1D11) and LAP (latency associated peptide) neutralizing antibodies (1 μg/mL, clone 27235) were obtained from R&D systems.

Statistical analysis: results from cytokine measurements are expressed as mean±SEM. DQ8d-specific proliferation, ear-thickness, and cytokine measurements were tested for significance using one-way ANOVA followed by the student's t-test comparison to determine the differences between individual groups. For all tests a P value <0.05 was used to indicate statistical significance.

Results

Suppression of the DTH and proliferative response by DQ8d-BLP. NOD AB° DQ8 transgenic mice were treated SLIT with DQ8d, BLP, DQ8d-BLP and DQ8d-BLP-VM (additional vitamin D3 and D-mannose) and PBS (as a negative control) for 10 consecutive days. On day 10, mouse ears were injected with 10 μg DQ8d and 24 hours later ear-thickness measurements were performed. Control mice (PBS) were clearly sensitized to DQ8d. Daily SLIT treatment of DQ8d-BLP significantly reduced the DTH response (P<0.05) over the entire test period. Ear swelling was also significantly reduced in DQ8d-BLP-VM treated mice compared to controls (P<0.01), however, there was no statistical significant difference with the DQ8d-BLP group. The DQ8d and BLP groups showed a slight reduction in the ear swelling, but this did not reach statistical significance compared to the PBS group. These data indicate that orally administered DQ8d-BLP with or without vitamin D3 and D-mannose suppresses systemic inflammatory T-cell responses in immunized NOD AB° DQ8 transgenic mice and that both the antigen and BLPs are necessary for induction of a significant tolerogenic effect.

Peripheral immune responses were further analyzed by investigating DQ8d-specific proliferation of spleen and draining cervical lymph node cells. Splenocytes of mice treated with PBS, BLP or DQ8-BLP or DQ8-BLP-VM were isolated on day 11 after SLIT, and the DQ8d-specific proliferative response was assessed by ex vivo stimulation with DQ8d peptide or irrelevant peptide. Splenocytes of sensitized mice showed a high DQ8d-specific proliferative response that was significantly suppressed by daily SLIT treatment of DQ8-BLP or DQ8-BLP-VM when compared to the control PBS treated mice again with a tendency of a better suppression in the DQ8-BLP-VM. No significant suppression was observed in the BLP group. However, the cervical lymph nodes are the primary antigen recognition site in this SLIT protocol; therefore, we also examined the proliferative capacity of these lymphocytes. Proliferation of cervical lymph node cells was significantly decreased in the DQ8d-BLP or DQ8d-BLP-VM treated groups as compared to the PBS treated group and there was no significant proliferation in the BLP group. Splenocytes and cervical lymph node cells did not show any proliferative response with addition of an irrelevant control peptide in all three treatment groups.

To determine if antigen-specific suppression exists in the lamina propria cells, these cells were isolated from mice SLIT treated with DQ8d-BLP, DQ8d-BLP-VM as well as mice treated with PBS alone or BLPs. These cells were then treated in vivo with medium, DQ8d, or an irrelevant control peptide. A high background of proliferation was observed in lamina propria cells in all three groups of treated mice. However, the proliferation was suppressed with the addition of the DQ8d peptide only in mice treated with DQ8d-BLP or DQ8d-BLP-VM. Proliferation in the lamina propria was not diminished with the addition of irrelevant control peptide. This demonstrates that in the lamina propria, the suppression induced by the SLIT treatment with DQ8d-BLP (-VM) is specific to DQ8d peptide.

To investigate the mechanisms behind the reduction of antigen-induced T cell proliferation, cytokine profiles of ex vivo stimulated splenocytes or inguinal lymph node cells were determined. Ex vivo DQ8d stimulated spleen cells showed a significant up-regulation of IL-10 and a down-regulation of IL-12 production only in the DQ8d-BLP and DQ8d-BLP-VM treated groups compared to the negative control (PBS). Moreover, DQ8d-BLP and DQ8d-BLP-VM treatment significantly reduced the DQ8d-induced IFN-γ production in the inguinal lymph nodes compared to the negative control (PBS) treated mice. There was no difference between the cytokine levels across treatment groups when we stimulated the splenocytes, inguinal lymph node cells with irrelevant peptide. Addition of irrelevant peptide also did not change the levels of IL-10 and IL-12p70 from the media in four treatment groups. Together, the proliferative and cytokine data indicate that DQ8d-BLP(-VM) SLIT treatment is able to suppress T-cell responses systemically in NOD AB° DQ8 transgenic mice in an antigen-specific manner.

Critical role for both TGF-β and IL-10 in DQ8d-BLP mediated suppression. The functional importance of TGF-β, IL-10, and LAP (membrane-associated TGF-β) for the DQ8d-specific splenic proliferative response of splenocytes from DQ8d-BLP and DQ8d-BLP-VM treated mice compared to the PBScontrol group was assessed using neutralizing antibodies. The individual neutralization of IL-10-, TGF-β- or LAP did not significantly interfere with the decreased splenic proliferative response of DQ8d-BLP and DQ8d-BLP-VM treated mice, but adding a combination of TGF-β and IL-10 neutralizing monoclonal antibodies completely abolished the decreased DQ8d-specific proliferative capacity of splenocytes. These data strongly suggest that the T-cell activation suppression mediated by DQ8d-BLP or DQ8d-BLP-VM treatment is dependent upon interplay between IL-10 and TGF-β.

Increase in Foxp3 expression by $CD4^+CD25^+$ and $CD4^+CD25^-$ T cells. To analyze the role of regulatory T cells (Tregs) in the induction of DQ8d-BLP or DQ8d-BLP-VM-induced tolerance, we investigated the expression of Foxp3 within the $CD4^+$ T cell population by FACS analysis. A significant increase in the number of $Foxp3^+$ $CD4^+CD25^+$ cells as well as $Foxp3^+CD4^+CD25^-$ cells was seen in the spleen of DQ8d-BLP and DQ8d-BLP-VM treated mice as compared to the control group (PBS), while BLP or DQ8d only groups did not show a significant increase in the number of Foxp3 CD4+ T cells. An increased number of $Foxp3^+$ $CD4^+CD25^-$ cells was also detected in the oral draining lymph node tissue of the DQ8d-BLP and DQ8d-BLP-VM treated mice as compared to the PBS, BLP or DQ8d treated mice, but not in the $CD4^+CD25^+$ population. These data suggest a strong association between the increase in $Foxp3^+$ T-cells and the suppression of the immune response to gliadin by the SLIT administration of DQ8d-BLP(-VM).

Conclusion

Here, we demonstrate that sublingual oral delivery (SLIT) of a deaminated gliadin peptide in the presence of BLPs induces suppression of systemic DQ8-specific T-cell responses in NOD AB° DQ8 transgenic mice and provides a method for the induction of DQ8d antigen-specific tolerance. The results were most pronounced when BLPs were co-formulated with vitamin D3 and D-mannose. Moreover, this approach provides a method to deliver the right antigens in an adequate manner to the oromucosal immune system in the context of a non-living bacterial particle and has the potential for being an effective and non-toxic treatment of celiac disease. Although here we have used here DQ8d-BLP to induce suppression of systemic DQ8-specific T-cell responses in NOD AB° DQ8 transgenic mice the same results will be obtained when using a DQ2.5 or DQ2.2 in similar animal models for these antigens.

TABLE 8

Antigens for inducing immune tolerance to in accordance with the invention.

| Diseases | Autoantigens | Targeted population | Clinic/Target organ |
|---|---|---|---|
| Guillain-Barre Syndrome | Gangliosides GM1 orGD1a | 1.5 per 100.000 | Muscle weakness caused by damaging the peripheral nervous system |
| Hashimoto's Thyroiditis | Thyroid peroxidase (TPO), thyroglobulin (Tg), also TSH-R | 0.3 to 1.2% | Fatigue, weight gain, depression, muscle weakness, cold sensitivity-Hypothyroidism |
| Juvenile idiopathic arthritis | Oncoprotein DEK | unknown | Inflammation in joints, lethargy and poor appetite |
| Microscopic polyangiitis | Myeloperoxidase (MPO) | 1 per 100.000 | Small vessels inflammation |
| Multiple sclerosis | Myelin basic protein, Myelin oligodendrocytic glycoprotein (MOG), Proteolipid protein, also α-enolase, Aquaporin-4, β-arrestin and S100β | 4.7 per 100.000 | Demyelination of nerve cells - damage of central nervous system |
| Myasthenia gravis | Nicotinic acetylcholine receptor (nAchR), muscle-specific kinase (MuSK) and LRP4 for 10 to 20% of patients | 5 to 20 per 100.000 | Neuromuscular disease that leading to skeletal muscle weakness |
| Systemic sclerosis | Sci70/DNA topoisomerase I, RNA polymerase III, U1-RNP, U3-RNP, Ro52 | 1 per 6500 | Overproduction of collagen - Fibrosis and vascular obliteration in the skin and organs |
| Systemic lupus erythematosus | Double-stranded DNA, Ro/Ssa, La/SSb, Nucleosomal histones and ribonucleoproteins (snRNP), Phospholipid-β-2 glycoprotein I complex, Poly(ADP-ribose) polymerase and Sm antigens of U-1 small ribonucleoprotein complex | 20 to 70 per 100.000 | Multi-organs. Joints, muscles, butterfly rash, inflammation of heart and lungs - Symptoms of fever and fatigue |
| Type I diabetes | IA-2 (50%), GAD-65 (>80%), ZnT8 (60-80%), IGRP, Chromogranin A | 250 per 100.000 | Pancreatic β cells destroyed, thus decreasing insulin production |
| Addison's disease | Steroidogenic 21-hydroxylase | 22 per 100.000 | Adrenal hormone insufficiency |
| Antiphospholid syndrome | β$_2$-glycoprotein I and (prothrombin) | 50 per 100.000 | Thrombosis in both arteries and veins |
| Bullous pemphigoid | BP180(>75%), BP230, (27%) and β4 integrin (21%) | 5 per 100.000 | Skin disease - Formation of bullae between epidermis and dermis |
| Celiac disease | Gliadin (α, γ, and ω) | 0.5 to 1% | Reaction to gluten causing damage to the small intestine |
| Cicatricial pemphigoid | BP180 and α3 subunit of Laminin 332 | unknown | Lesions in the gingiva or gums |
| Eosinophilic granulomatosis with polyangiitis | Myeloperoxidase | 1 per 70.000 | Small vessels inflammation |
| Goodpasture's syndrome | NC1 domain of the alpha 3 chain of type IV collagen | 0.18 per 100.000 | Attack of the basement membrane in lungs and kidneys |
| Granulomatosis with polyangiitis | Proteinase 3 (PR3) | 3 per 100.000 | Small vessels inflammation |
| Grave's disease | Thyroid stimulating hormone receptor (TSH-R) | 0.5 to 3% | weakness, sleeping problems, diarrhea and unintentional weight loss |
| Myositis: | Jo-1, POL-7, PL-12 | 1 per 25 000 | Inflammatory myopathy |
| Antisynthetase Syndrome | Mi2, Tif1γ, MDAS | 1 per 50 000 | Skin and muscle lesions |
| Dermatomyositis | CN1a | 1 per 100 000 | Atrophy of specific muscle |
| Inclusion body myositis Necrotizing myopathy | HMGCR, SRP | 300 cases to date | Limb muscle weakness |
| Neuromyelitis optica | Aquaporin-4 in 73% of NMO patients, MOG in 7% of patients | 0.52 to 4 per 100 000 | Loss of vision and spinal cord function |
| Pemphigus vulgaris | Desmoglein (DSG(3 and DSG 1 | 9.48 per 100 000 (Germany) 40 000 in US | Blistering of oral (buccal and palatine mucosa) and skin (groin, abdomen) surfaces |
| Rheumatoid arthritis | Rheumatoid factor (RF; Fc portion of IgG), | 0.5 to 1% | Primarily affect joints that become swollen tender, and warm. |
| Sjogren's syndrome | Ro52, Ro60, La/SSb and α-fodrin | 0.2% | Dry mouth and Dry eyes |
| Stiff person syndrome | Glutamic acid decarboxylase (GAD) | 0.1 per 100 000 | Progressive rigidity and stiffness - Neurologic disorder |

The invention claimed is:

1. A method for inducing immune tolerance in a subject, the method comprising administering to the oral mucosa of the subject a mucoadhesive carrier wherein the mucoadhesive carrier is a mucoadhesive patch comprising mucoadhesive nanofibers incorporating or loaded with a non-living bacterial particle and an antigen-containing extract or wherein the mucoadhesive carrier is a hydrogel or film of water swellable, cross-linked mucoadhesive polymers that are impregnated or loaded with the bacterial particle and the extract, and wherein the non-living bacterial particle is derived from a probiotic bacterium selected from:
   a) a heat-treated Gram-positive bacterium;
   b) a chemically sterilized bacterium.

2. The method according to claim 1, wherein at least one antigen in the antigen-containing extract causes or is associated with an immune response related disease.

3. The method according to claim 2, wherein the immune response related disease is chosen from the group consisting of celiac disease, allergic asthma, allergic rhinitis, allergic conjunctivitis, atopic dermatitis, multiple sclerosis, type I diabetes, autoimmune uveitis, autoimmune thyroiditis, autoimmune myasthenia gravis, rheumatoid arthritis, pemphigus vulgaris or food allergy.

4. The method according to claim 1, wherein the antigen-containing extract is obtained from pollen, gluten, house dust mite, cat saliva, birch or peanut.

5. The method according to claim 1, wherein the antigen-containing extract comprises at least one immunodominant epitope selected from the group consisting of immunodominant epitopes of a-gliadin, hordein, house dust mite, and peptides from cat saliva, skin or glands.

6. The method according to claim 5, wherein the immunodominant epitope of house dust mite is Der p 2.1 and the immunodominant epitope of peptides from cat saliva, skin or glands is Feld 1.

7. The method according to claim 6, wherein:
   a) the heat-treated Gram-positive bacterium is *L. lactis;*
   b) the chemically sterilized bacterium is *L. lactis, Lb. rhamnosus,* or *E. coli* Nissle.

8. The method according to claim 1, wherein the mucoadhesive carrier is a patch comprising electrospun fibers.

9. The method according to claim 8, wherein the probiotic bacterium is a *Lactobacillus*, a *Lactococcus*, a *Bifidobacterium* or an *Escherichia coli* Nissle.

10. The method according to claim 1, wherein the subject is a human or an animal.

* * * * *

SEQUENCE LISTING

```
Sequence total quantity: 4
SEQ ID NO: 1            moltype = AA  length = 9
FEATURE                 Location/Qualifiers
REGION                  1..9
                        note = Gliadin alpha1 peptide
source                  1..9
                        mol_type = protein
                        organism = synthetic construct
SEQUENCE: 1
PFPQPELPY                                                                 9

SEQ ID NO: 2            moltype = AA  length = 9
FEATURE                 Location/Qualifiers
REGION                  1..9
                        note = Gliadin alpha2 peptide
source                  1..9
                        mol_type = protein
                        organism = synthetic construct
SEQUENCE: 2
PQPELPYPQ                                                                 9

SEQ ID NO: 3            moltype = AA  length = 33
FEATURE                 Location/Qualifiers
REGION                  1..33
                        note = Gliadin 33-mer alpha2 peptide
source                  1..33
                        mol_type = protein
                        organism = synthetic construct
SEQUENCE: 3
LQLQPFPQPE LPYPQPELPY PQPQLPYPQP QPF                                     33

SEQ ID NO: 4            moltype = AA  length = 31
FEATURE                 Location/Qualifiers
REGION                  1..31
                        note = DQ8d peptide
source                  1..31
                        mol_type = protein
                        organism = synthetic construct
SEQUENCE: 4
GAPVPYPDPL EPRQYPSGEG SFQPSQENPQ A                                       31
```